United States Patent
Gloth

[11] Patent Number: 5,813,973
[45] Date of Patent: Sep. 29, 1998

[54] DEVICE AND METHOD FOR ALLEVIATING FEMALE URINARY INCONTINENCE

[76] Inventor: David Gloth, 16 Harcourt St., #6I, Boston, Mass. 02116

[21] Appl. No.: 641,160

[22] Filed: May 30, 1996

[51] Int. Cl.⁶ .................................................. A61B 19/00
[52] U.S. Cl. ............................................................ 600/29
[58] Field of Search ................... 128/760–769, 128/885, 883, DIG. 25; 600/29–32, 573–582

[56] References Cited

U.S. PATENT DOCUMENTS

| | | |
|---|---|---|
| 3,340,876 | 9/1967 | Hill . |
| 3,349,768 | 10/1967 | Keane . |
| 3,512,185 | 5/1970 | Ellis . |
| 3,661,155 | 5/1972 | Lindan . |
| 3,683,914 | 8/1972 | Crowley . |
| 3,705,575 | 12/1972 | Edwards . |
| 3,776,235 | 12/1973 | Ratcliffe et al. . |
| 3,958,564 | 5/1976 | Langguth . |
| 4,019,498 | 4/1977 | Hawtrey et al. ........................... 600/29 |
| 4,139,006 | 2/1979 | Corey ......................................... 600/29 |
| 4,194,508 | 3/1980 | Anderson . |
| 4,256,093 | 3/1981 | Helms et al. . |
| 4,421,511 | 12/1983 | Steer et al. . |
| 4,484,917 | 11/1984 | Blackmon . |
| 4,496,355 | 1/1985 | Hall et al. . |
| 4,563,183 | 1/1986 | Barrodale et al. . |
| 4,690,677 | 9/1987 | Erb . |
| 4,795,449 | 1/1989 | Schneider et al. . |
| 4,822,347 | 4/1989 | MacDougall . |
| 4,846,819 | 7/1989 | Welch . |
| 4,889,532 | 12/1989 | Metz et al. . |
| 4,904,248 | 2/1990 | Vaillancourt . |
| 5,036,867 | 8/1991 | Biswas ....................................... 600/30 |
| 5,074,855 | 12/1991 | Rosenbluth et al. . |
| 5,090,424 | 2/1992 | Simon et al. . |
| 5,131,906 | 7/1992 | Chen . |
| 5,195,997 | 3/1993 | Carns . |
| 5,263,947 | 11/1993 | Kay . |
| 5,336,208 | 8/1994 | Rosenbluth et al. . |

FOREIGN PATENT DOCUMENTS

| | | |
|---|---|---|
| 947602 | 5/1974 | Canada . |
| 1223.353 | 6/1960 | France . |
| 2 542 995 | 3/1983 | France . |
| 28 17 571 | 10/1978 | Germany . |
| 3633824 A1 | 4/1988 | Germany . |
| 1467144 | 3/1977 | United Kingdom . |
| 2193438 | 2/1988 | United Kingdom . |
| WO 90/08561 | 8/1990 | WIPO . |
| WO9639989 | 12/1996 | WIPO . |
| WO9639991 | 12/1996 | WIPO . |

OTHER PUBLICATIONS

Richardson et al., "Reproducibility of Pressure Transmission Ratios in Stress Incontinent Women", Neurourology and Urodynamics 12:123–130 (1993).

*Primary Examiner*—John P. Lacyk
*Assistant Examiner*—Samuel Gilbert
*Attorney, Agent, or Firm*—Judith C. Crowley; Nutter, McClennen & Fish LLP

[57] ABSTRACT

A device for alleviating female urinary incontinence comprising a device body and a urethra obstructing member. The device body forms a cavity. The urethra obstructing member is shaped to deform the user's urethra and to cause the user's urethra to be substantially obstructed. When the device is positioned on a user's body, a partial compression of the device body produces a vacuum within the cavity which is sufficient to hold the device onto the user's body. The device may be re-usable, non-reusable or of limited re-use.

62 Claims, 24 Drawing Sheets

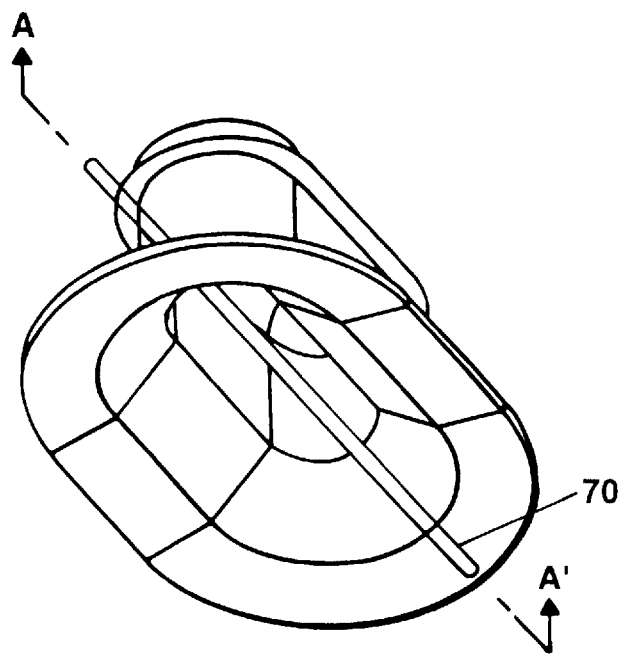
*Figure 13A*
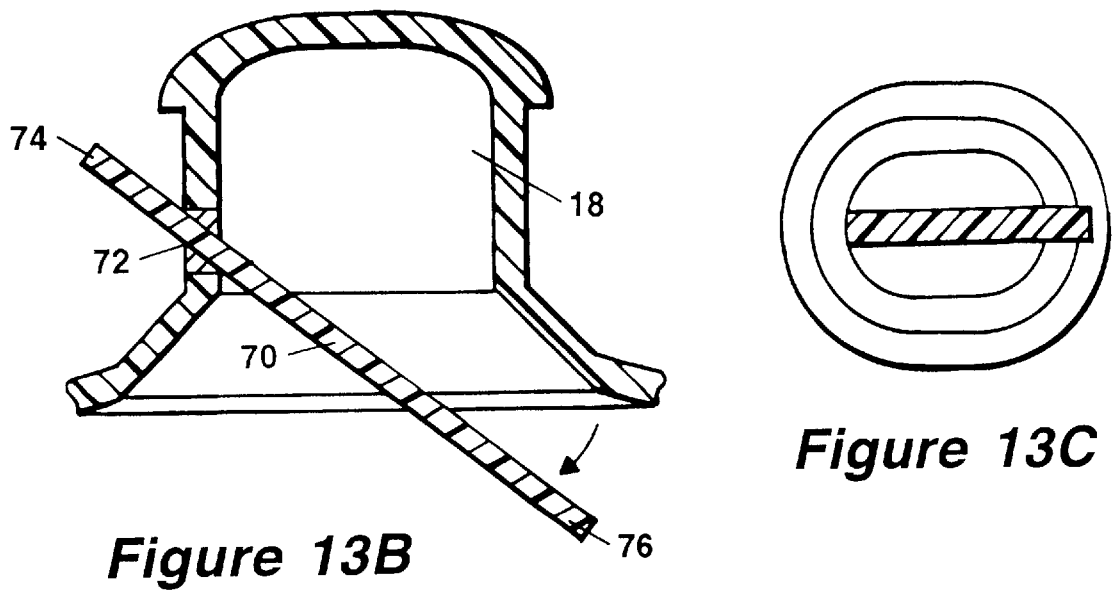
*Figure 13B*
*Figure 13C*

DEVICE AND METHOD FOR ALLEVIATING FEMALE URINARY INCONTINENCE

FIELD OF THE INVENTION

The invention relates generally to a device and method for alleviating female urinary incontinence and more specifically to a device and method which obstruct the urethra to alleviate female urinary incontinence.

BACKGROUND OF THE INVENTION

Urinary incontinence is the involuntary loss of urine. In women, stress incontinence, which is the involuntary loss of urine with mild physical stress such as coughing, laughing, running or lifting, is the most common form of urinary incontinence. Urinary incontinence in women can be caused by a variety of physical and mental factors. Injuries sustained during childbirth, trauma to the urethra or bladder neck, and neurogenic bladder dysfunction can all cause urinary incontinence in women.

Many of the devices designed to alleviate female urinary incontinence involve catheters or balloons which must be positioned internally when the device is in use. Several disadvantages exist with these devices. Such devices may cause infection, be uncomfortable to wear, inconvenient to use, and expensive. Other devices designed to alleviate female urinary incontinence are pessaries which, when placed in the vagina near the cervix, elevate the bladder neck. Pessaries can be uncomfortable to wear and difficult to place on the body.

As shown in FIGS. 1A–1D, one device for alleviating female urinary incontinence that is designed to be applied externally is the female urinary incontinence device described in U.S. Ser. No. 08/578,031 now abandoned. As described, the device has a resilient and at least partially deformable body with a hand gripping portion. The body is deformed to produce a vacuum within the chamber to hold the device on the user's body and, is positioned over the user's meatus to constrict the meatus to alleviate urinary incontinence. However, this device may not supply enough vacuum to adequately constrict the meatus and sufficiently prevent female urinary incontinence in all patients. Furthermore, the device is reusable and therefore places the patient at increased risk of bladder contamination and urinary tract infections.

The present invention addresses these problems and provides a female urinary incontinence device which further alleviates female urinary incontinence.

SUMMARY OF THE INVENTION

The invention relates to a device for alleviating female urinary incontinence. The device has a body which forms a cavity and a urethra obstructing member. The urethra obstructing member is shaped to deform the user's urethra and to cause the user's urethra to be substantially obstructed. The device is held in place by a differential in air pressure. When the device is positioned on the user's body, a partial compression of the device's body produces a vacuum within the body cavity of the device which is sufficient to hold the device onto the user's body. In one embodiment, one end of the urethra obstructing member is attached to the internal surface of the device's body while the other end of the urethra obstructing member extends from the device's body to press against the distal portion of the user's urethra to substantially obstruct the urethra. In other embodiments the urethra obstructing member is shaped to cause the user's urethra to be completely obstructed.

In other embodiments, with or without the urethra obstructing member, the device is non-reusable or has limited re-use. In one non-reusable embodiment, a communication between the device body's cavity and the exterior of the device's body is created when the user removes the device from the user's body. In another non-reusable embodiment, the device has interlocking members within the device body's cavity which prevent re-expansion of the device's body after the first use. In another non-reusable embodiment, the device includes an inflatable balloon apparatus which prevent recompression of the device's body after the first use.

The invention also relates to a method for alleviating female urinary incontinence. The method includes the steps of applying a urinary incontinence device having a body which forms a cavity and urethra obstructing member onto the user's body and compressing the device's body to produce a vacuum within the body cavity of the device to hold the device onto the user's body. In one embodiment the device is placed over the orifice of the user's urethra. In another embodiment the device is placed on the anterior vaginal wall along the path of the urethra. Once the device is in place, the urethra obstructing member presses against the distal portion of the user's urethra to substantially obstruct the urethra and alleviate urinary incontinence.

In another embodiment, the user is able to control the amount of vacuum applied to the user's meatus by the urinary incontinence device. The amount of vacuum produced by the device depends on the volume within the body cavity of the device. The user can vary the amount of vacuum applied to the meatus by varying the compression of the device's body upon placement of the device on the user's body. In another embodiment, the device has internal protuberances which regulate the amount of volume within the device body's cavity and, therefore, regulate the amount of vacuum applied to the meatus.

BRIEF DESCRIPTION OF THE DRAWINGS

This invention is pointed out with particularity in the appended claims. The above and further advantages of this invention may be better understood by referring to the following description taken in conjunction with the accompanying drawings, in which:

FIG. 13A is a perspective view of an embodiment of a female urinary incontinence device having an oval-shaped device body defining a cavity and lever extending through the cavity to act as a urethra obstructing member;

FIG. 13B is a cross-sectional view of the device of FIG. 13A taken through line A-A' of FIG. 13A;

FIG. 13C is a bottom view of the device of FIG. 13A;

Like reference characters in the respective drawn figures indicate corresponding parts.

DETAILED DESCRIPTION OF THE INVENTION

Figure 1B:
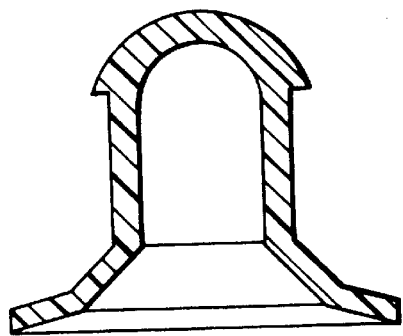
FIG. 1B is a cross-sectional view of the device of FIG. 1A taken through line A-A' of FIG. 1A.
Figure 1C:
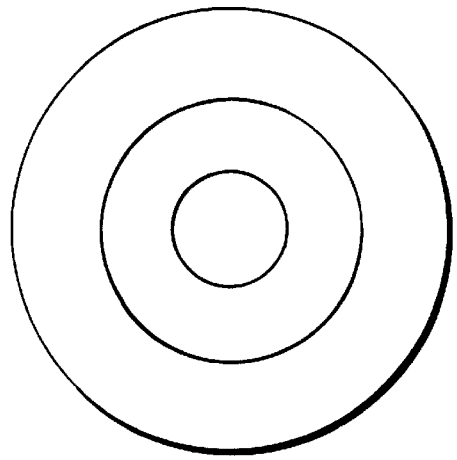
FIG. 1C is a bottom view of the device of FIG. 1A.
Figure 1D:
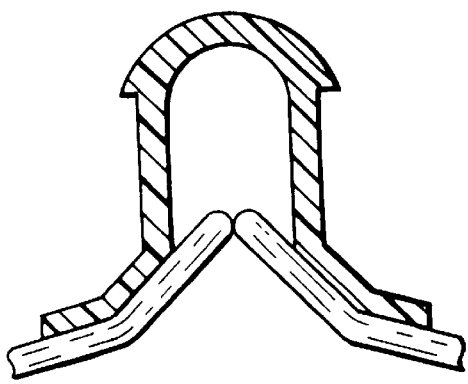
FIG. 1D is a cross-sectional view taken through line A-A' of FIG. 1A of the device of FIG. 1A when in place on the body of a user.
Figure 1A:
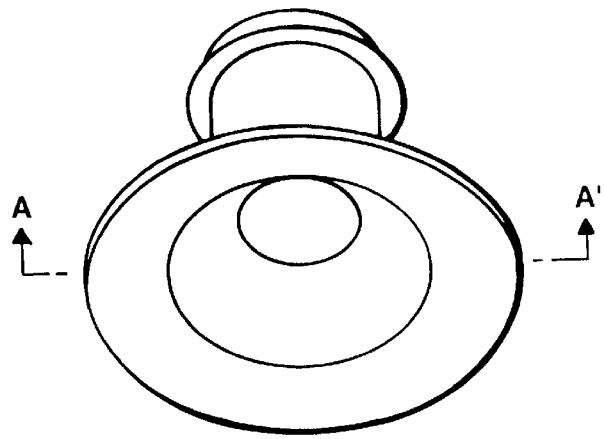
FIG. 1A is a perspective view of a prior art female urinary incontinence device having a circular body defining a cavity.
Figure 2A:
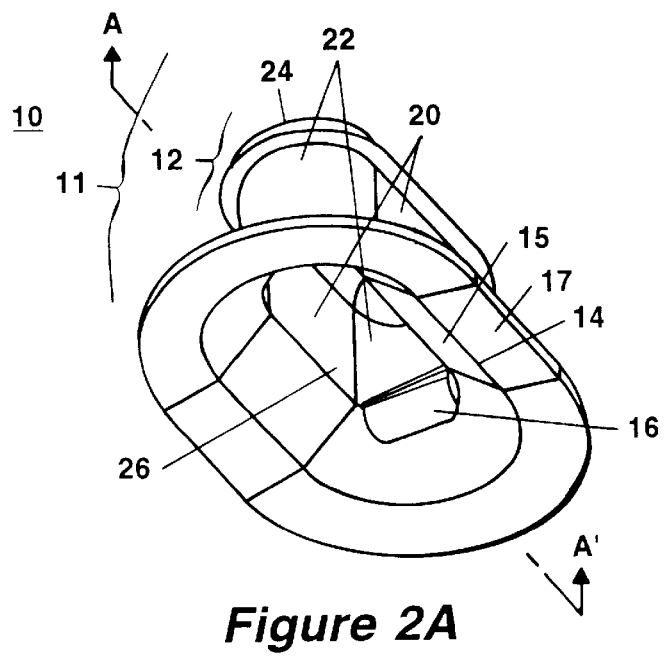
FIG. 2A is a perspective view of an embodiment of a female urinary incontinence device having an oval-shaped device body defining a cavity and a urethra obstructing member attached to and extending from the device body.
Figure 2B:
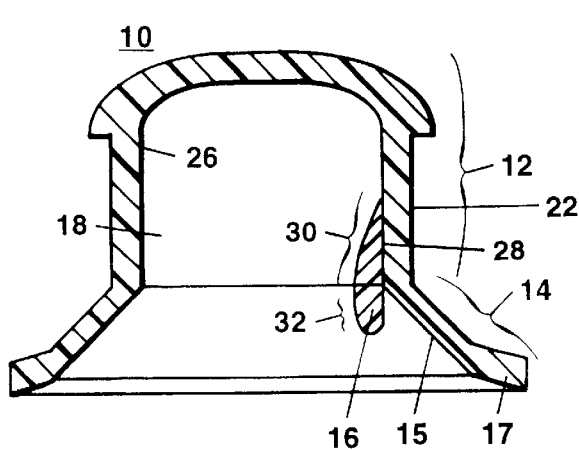
FIG. 2B is a cross-sectional view of the device of FIG. 2A taken through line A-A' of FIG. 2A.
Figure 2C:
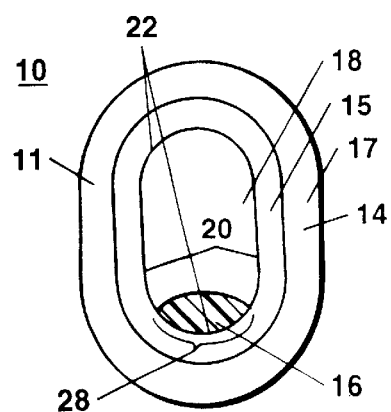
FIG. 2C is a bottom view of the device of FIG. 2A.

In broad overview and referring to FIGS. 2A, 2B and 2C, an embodiment of a female urinary incontinence device 10 of the invention, as shown in perspective view, cross-sectional view and bottom view in the respective Figures, includes a device body 11 and a urethra obstructing member 16. Device body 11 defines a cavity 18 and has a vacuum producing portion 12 and a body contacting portion 14. Body contacting portion 14 has an intermediate frustoconical portion 15 and an encircling rim 17. Typically, female urinary incontinence device 10 is a unitary part formed out of one piece of material. However, device 10 may be formed out of multiple pieces of material joined together. Device body 11 may be made of any resilient and partially flexible material that is suitable for application to the human body over the meatus urinarius. Urethra obstructing member 16 may be made of any rigid or resilient material that is suitable for contacting the skin surrounding the meatus urinarius and that is sufficiently firm to apply ample pressure to the distal urethra to substantially obstruct the urethra and alleviate urinary incontinence. In the preferred embodiment, device body 11 and urethra obstructing member 16 are composed of FDA approved silicone rubber. In other embodiments, device body 11 and urethra obstructing member 16 are composed of urethene or thermoplastic elastomers. In another embodiment, device body 11 and urethra obstructing member 16 may be composed of two different grades of FDA approved silicone rubber having different stiffness. Urethra obstructing member 16 will be discussed in more detail below.

The purpose of vacuum producing portion 12 is to produce a vacuum within the device body's cavity 18 to hold the female urinary incontinence device 10 onto the user's body. The vacuum producing portion 12 may come in many different sizes and shapes. FIGS. 2A–2C show the vacuum producing portion 12 having an elliptical shape with substantially vertical side walls 20, substantially vertical end walls 22, and ceiling 24. Once the device 10 is positioned over the user's body, a vacuum may be produced in the device body's cavity 18 by squeezing vacuum producing portion 12. The device 10 may be positioned over the user's meatus or on the user's anterior vaginal wall along the path of the urethra. In one embodiment, vacuum producing portion 12 has a length of approximately ⅞ inch, a width of approximately ⅜ inch, and a height of approximately 1 inch. It is preferred that the material used for vacuum producing portion 12 is resilient enough that vacuum producing portion 12 can be compressed by light hand pressure.

Figure 3B:
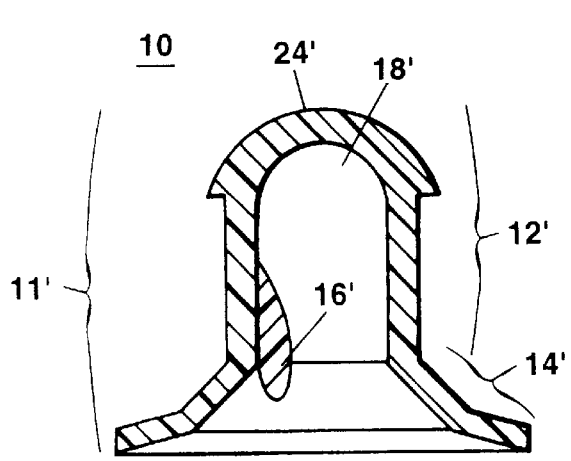
FIG. 3B is a cross-sectional view of the device of FIG. 3A taken through line A-A' of FIG. 3A.
Figure 3C:
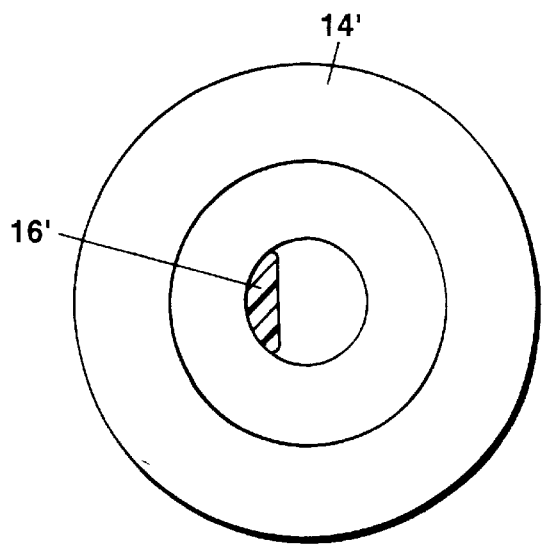
FIG. 3C is a bottom view of the device of FIG. 3A.
Figure 3A:
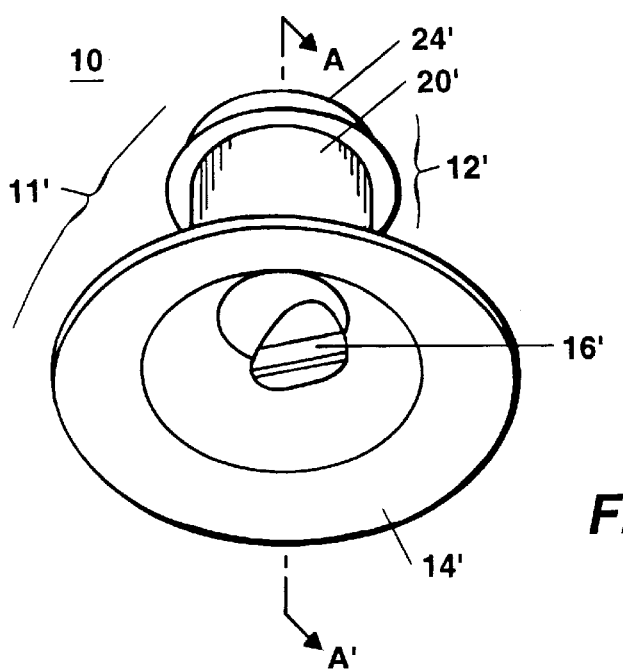
FIG. 3A is a perspective view of an embodiment of a female urinary incontinence device having a circular device body defining a cavity and a urethra obstructing member attached to and extending from the device body.

FIGS. 3A–3C show the vacuum producing portion 12' having a circular shape with a substantially vertical wall 20' and ceiling 24'. As in the elliptical-shaped embodiment of FIGS. 2A–2C, a vacuum may be produced within the device body's cavity 18' by squeezing the vacuum producing portion 12'.

Figure 4A:
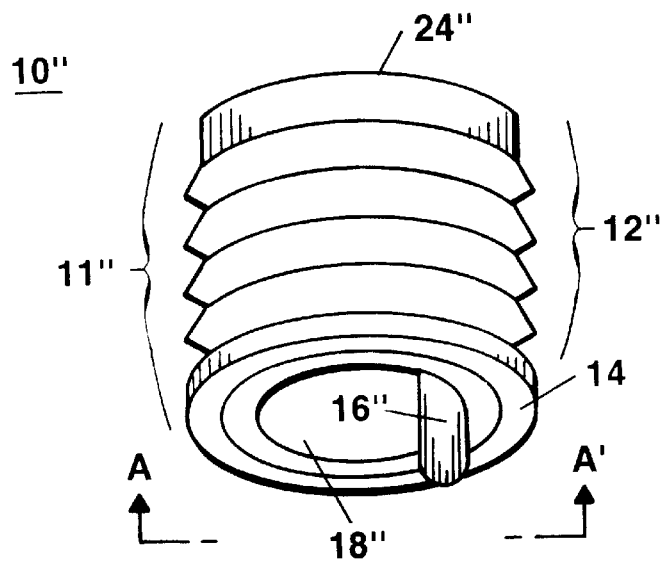
FIG. 4A is a perspective view of an embodiment of a female urinary incontinence device having an accordion-shaped device body defining a cavity and a urethra obstructing member attached to and extending from the device body.
Figure 4B:
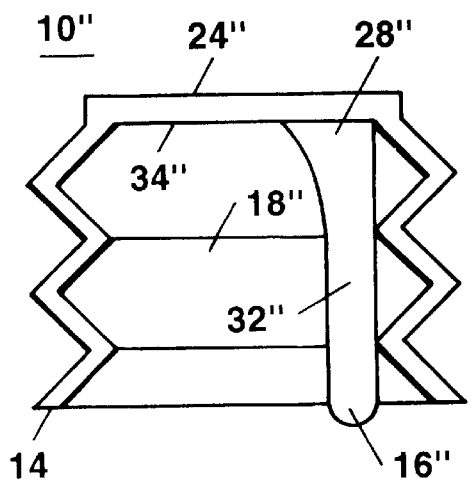
FIG. 4B is a cross-sectional view of the device of FIG. 4A taken through line A-A' of FIG. 4A.
Figure 4C:
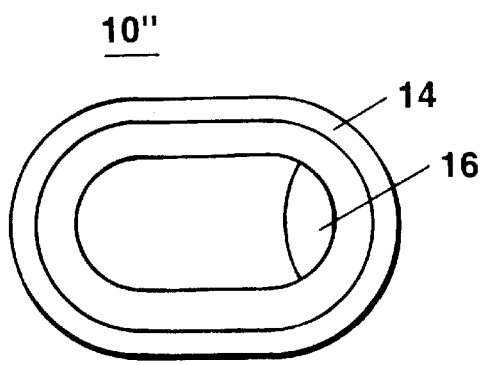
FIG. 4C is a bottom view of the device of FIG. 4A.

FIGS. 4A–4C show vacuum producing portion 12" having an accordion shape. A vacuum may be produced within the device body's cavity 18" by pressing down on the ceiling 24" of vacuum producing portion 12" once the device 10 is positioned over the user's meatus or on the user's anterior vaginal wall along the path of the urethra. The vacuum producing portion 12 can also be square, bulbous, or any other shape so long as the device body's cavity 18 has adequate volume to allow a vacuum to be formed within the device body's cavity 18 sufficient to hold the device 10 onto the user's body and so long as the shape does not cause user discomfort. The ceiling 24 of the vacuum producing portion 12 can be flat, rounded, or any other shape that closes the device body's cavity 18. The vacuum producing portion 12 must be made out of a resilient material in order to maintain a sufficient degree of suction to hold the device 10 onto the user's body.

Figure 5A:
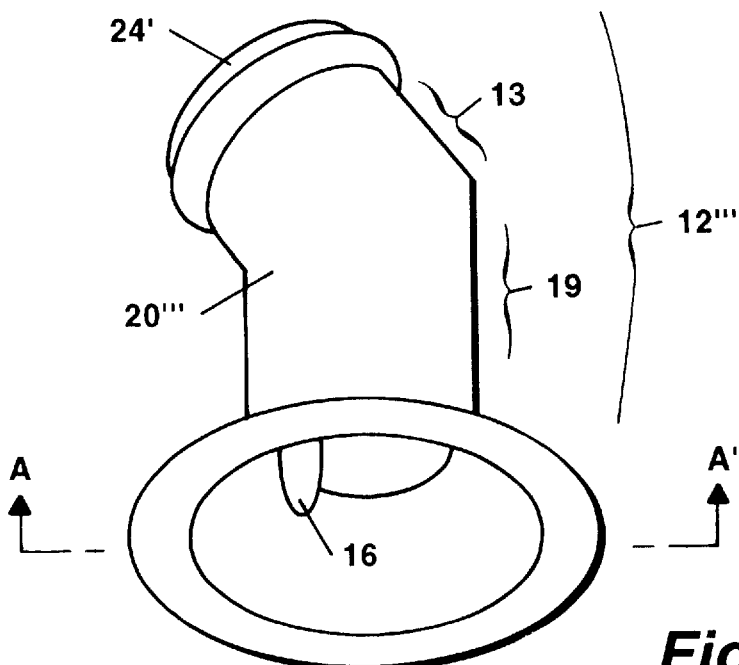
FIG. 5A is a perspective view of an embodiment of a female urinary incontinence device having a bent circular device body defining a cavity and a urethra obstructing member attached to and extending from the device body.
Figure 5B:
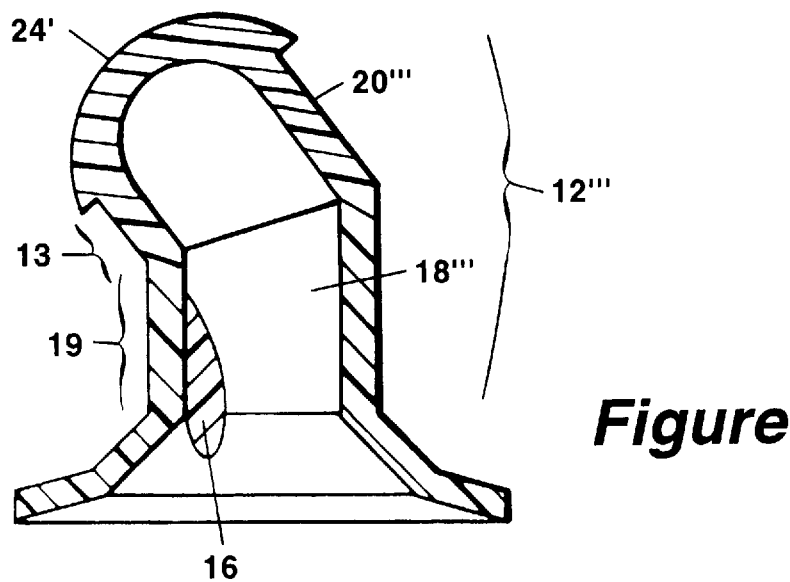
FIG. 5B is a cross-sectional view of the device of FIG. 5A taken through line A-A' of FIG. 5A.

FIGS. 5A and 5B show vacuum producing portion 12''' having a substantially circular shape with an angled side wall 20''' and ceiling 24'. In one embodiment, the vacuum producing portion 12''' is angled toward the urethra obstructing member 16. In another embodiment the top portion 13 of the vacuum producing portion 12''' is attached to the bottom portion 19 of the vacuum producing portion 12''' at an angle of 30 degrees. As in the circular shape embodiment of FIGS. 3A–3C, a vacuum may be produced within the device body's cavity 18''' by squeezing the vacuum producing portion 12'''.

Attached and adjacent to the vacuum producing portion 12 is a body contacting portion 14. Body contacting portion 14 has an intermediate frustoconical portion 15 and an encircling rim 17. Both the intermediate frustoconical portion 15 and encircling rim 17 contact the user's skin. FIGS. 2A–2C show the body contacting portion 14 having an elliptical shape. In one embodiment the device has a length of approximately 1¾ inches and a width of approximately 1⅜ inches. In a second embodiment shown in FIGS. 3A–3C, the body contacting portion 14' has a circular shape. In one embodiment, the body contacting portion 14' has an inner diameter of approximately ⅜ inch and an outer diameter of approximately 1⅜ inches. The body contacting portion 14 may also be any other shape that provides a complete seal between the user's body and the female urinary incontinence device 10. The body contacting portion 14 is made of a flexible material to provide a continuous and complete seal between the user's body and the device 10. The body contacting portion 14 is capable of sealing the urinary incontinence device 10 to the user's body and preventing any air from entering the device body's cavity 18 or fluid from escaping the device body's cavity 18. A sealing material or lubricant may be applied to the body contacting portion 14 to more securely seal the device 10 to the user's body.

Attached to the device body 11 is the urethra obstructing member 16 discussed above. While the urethra obstructing member 16 is described as a separate piece, it may also be integral with device body 11. The urethra obstructing member 16 may be many different shapes and sizes. The urethra obstructing member 16 is shaped and sized to effectively deform the user's distal urethra to cause the user's urethra to be sufficiently obstructed to alleviate urinary incontinence. In one embodiment, the urethra obstructing member 16 completely obstructs the user's urethra. Referring to FIGS. 2A–2C, the urethra obstructing member 16 has a device body contacting portion 30 and a pressure applying portion 32 which presses against the user's distal urethra to obstruct the urethra. Urethra obstructing member 16 may be rigid or flexible, however, it must be sufficiently firm to apply ample pressure to the user's distal urethra to substantially obstruct the urethra. The device body contacting portion 30 has a preferred length of ¼ inch and is attached to or integral with the internal surface 26 of the vacuum producing portion 12. In other embodiments, the device body contacting portion 30 may extend downward along and be attached to a portion of the intermediate frustoconical portion 15. In one embodiment, the pressure applying portion 32 of urethra obstructing member 16 has a length preferably in the range of ⅛ inch to ½ inch with ⅛ inch being preferred and extends from the device body 11 to press against the distal portion of the user's urethra to substantially obstruct the urethra.

In the embodiment shown in FIGS. 2A–2C, the device body contacting portion 30 of the urethra obstructing member 16 is attached along and adjacent to one of the substantially vertical end walls 22 of the vacuum producing portion 12. In this embodiment, the surface 28 of the device body contacting portion 30 that is attached to end wall 22 conforms to the rounded shape of end wall 22 and extends along only a portion of the length of end wall 22. In other embodiments, surface 28 may extend the entire length of end wall 22. In still other embodiments, surface 28 may not conform to the shape of end wall 22, but may be attached to end wall 22 only at certain points. In other embodiments surface 28 may be flat and may be attached adjacent to one of the substantially vertical side walls 20.

In another embodiment of the present invention as shown in FIGS. 4A–4C, the urethra obstructing member 16" is attached to the internal surface 34" of the ceiling 24" of the vacuum producing portion 12". In one embodiment of the present invention as shown in FIGS. 4A–4C, the urethra obstructing member 16" has a length of approximately one inch, protrudes from the internal surface 34" of the ceiling 24" and when compressed or in position on the user's body, extends beyond the plane of the body contacting portion 14" by a distance in the range of ⅛ inch to ½ inch with ⅛ inch being preferred. In another embodiment the urethra obstructing member 16" forms the ceiling 24" of the vacuum producing portion 12".

Figure 6A:
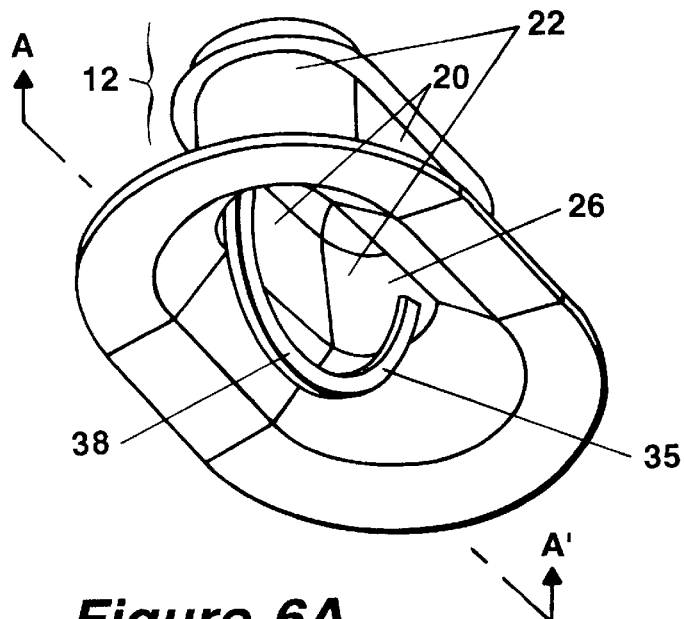
FIG. 6A is a perspective view of an embodiment of a female urinary incontinence device having an oval-shaped device body defining a cavity and a urethra obstructing member attached to the internal surface of the device body and extending across the device body's cavity.
Figure 6B:
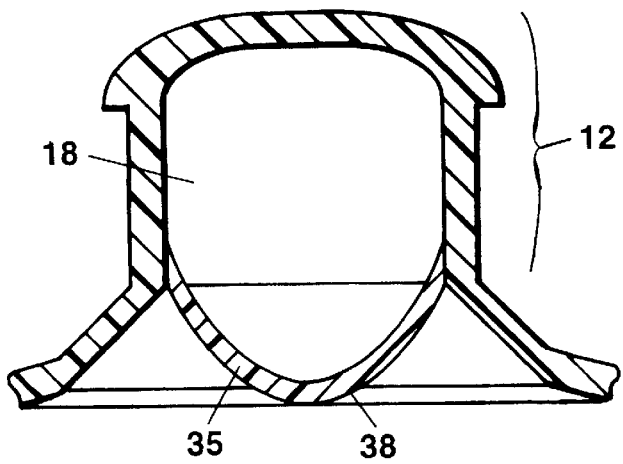
FIG. 6B is a cross-sectional view of the device of FIG. 6A taken through line A-A' of FIG. 6A.
Figure 6C:
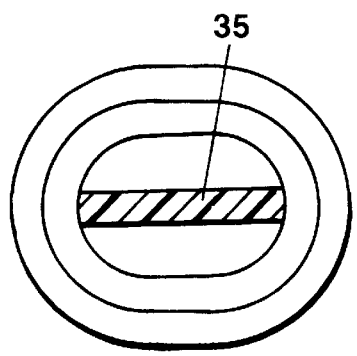
FIG. 6C is a bottom view of the device of FIG. 6A.
Figure 7A:
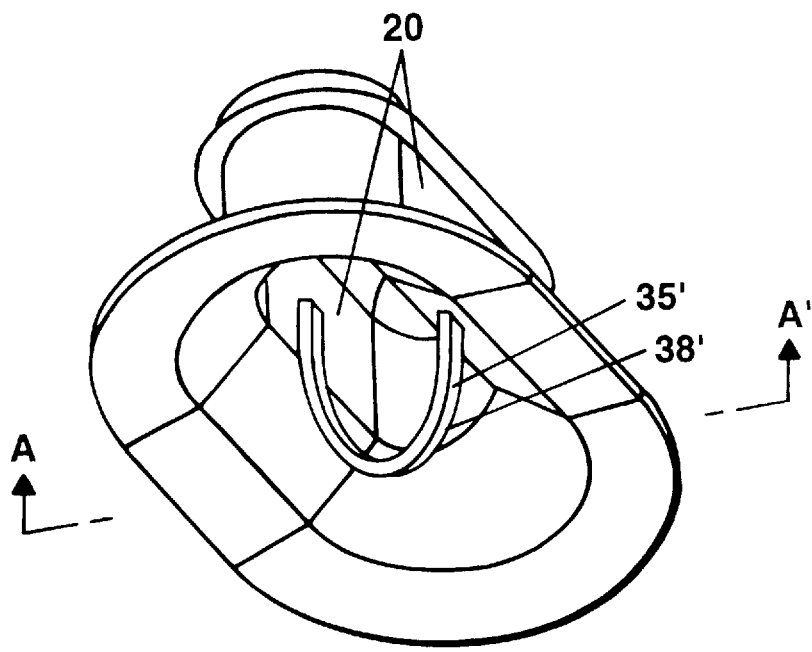
FIG. 7A is a perspective view of an embodiment of a female urinary incontinence device having an oval-shaped device body defining a cavity and a urethra obstructing member attached to the internal surface of the device body and extending across the device body's cavity.
Figure 7B:
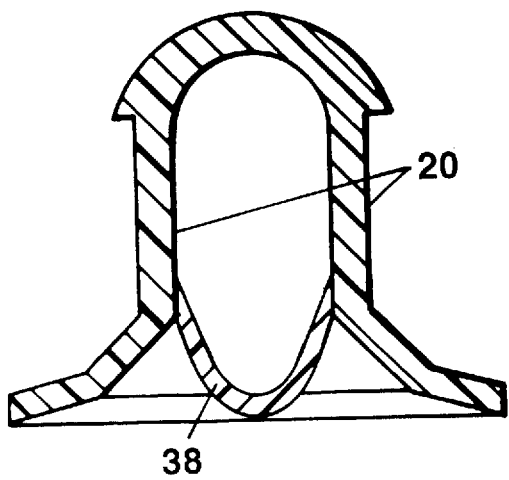
FIG. 7B is a cross-sectional view of the device of FIG. 7A taken through line A-A' of FIG. 7A.
Figure 7C:
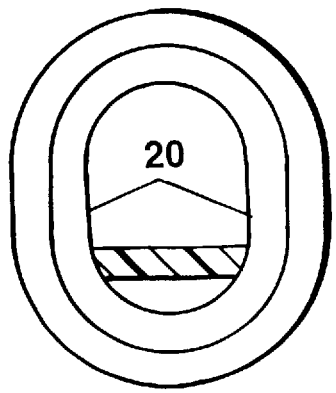
FIG. 7C is a bottom view of the device of FIG. 7A.

FIGS. 6A–6C show yet another embodiment of the urethra obstructing member 35 as a partially flexible and resilient member that is attached to the internal surface 26 of the vacuum producing portion 12 and extends from one side of the device body's cavity 18 to the other side of the device body's cavity 18. FIGS. 6A–6C show the urethra obstructing member 35 positioned parallel to the major axis of the elliptical vacuum producing portion 12. FIGS. 7A–7C show still yet another embodiment of the urethra obstructing member 35' as extending from one of the substantially vertical side walls 20 to the other substantially vertical side wall 20 across the device body's cavity 18 parallel to the minor axis of the elliptical vacuum producing portion 12. In other embodiments, the urethra obstructing member 35' can be attached anywhere along the side walls 20. FIGS. 7A–7C show urethra obstructing member 35' as being perpendicular to the side walls 20, however in other embodiments, it may be attached to side walls 20 at an angle.

Figure 8A:
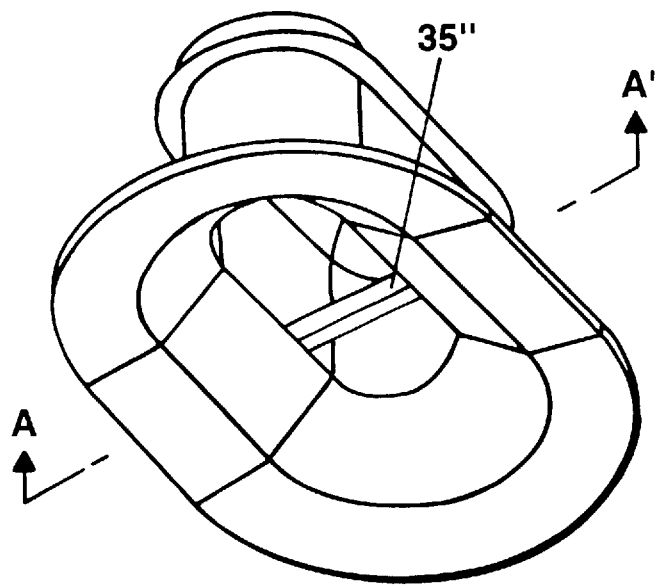
FIG. 8A is a perspective view of an embodiment of a female urinary incontinence device having an oval-shaped device body defining a cavity and a urethra obstructing member attached to the internal surface of the device body and extending across the device body's cavity.
Figure 8B:
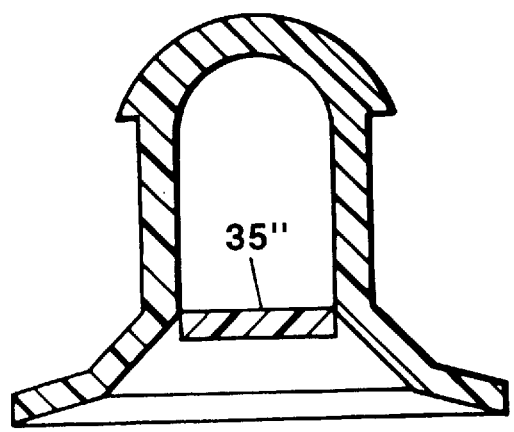
FIG. 8B is a cross-sectional view of the device of FIG. 8A taken through line A-A' of FIG. 8A.

In the embodiments shown in FIGS. 6A–6C and 7A–7C, the urethra obstructing members 35 and 35' have a semicircular shape and the body contacting surfaces 38 and 38' respectively of the urethra obstructing members 35 and 35' are flat. FIGS. 8A and 8B show an embodiment of urethra obstructing member 35" having a linear shape. In other embodiments, the urethra obstructing member may be parabolic or any other shape that is designed to apply pressure to the distal portion of the user's urethra. Also, the body contacting surface 38 of the urethra obstructing member 35 may be rounded rather than flat.

Figure 9A:
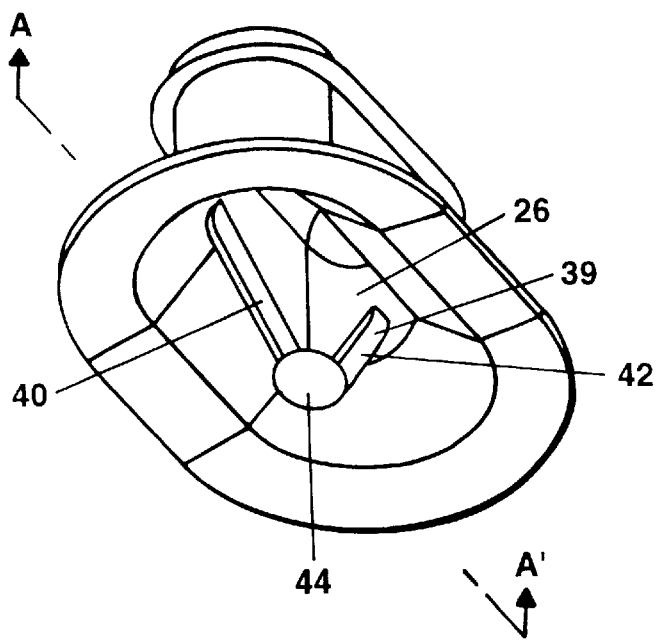
FIG. 9A is a perspective view of an embodiment of a female urinary incontinence device having an oval-shaped device body defining a cavity and a urethra obstructing member having a substantially linear portion and a pressure application member.
Figure 9B:
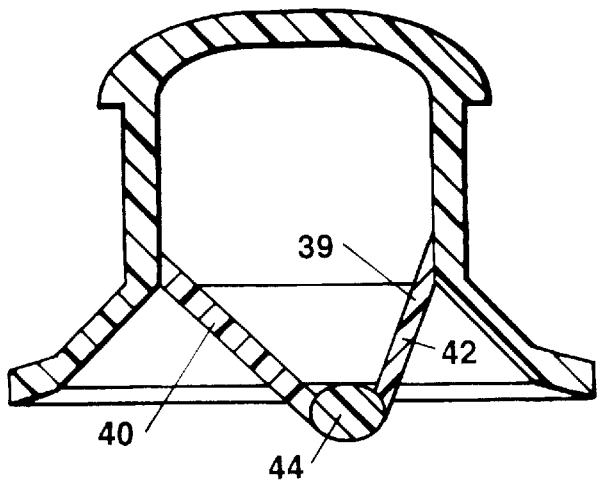
FIG. 9B is a cross-sectional view of the device of FIG. 9A taken through line A-A' of FIG. 9A.
Figure 9C:
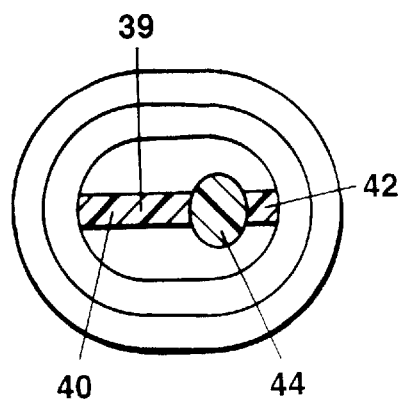
FIG. 9C is a bottom view of the device of FIG. 9A.
Figure 10A:
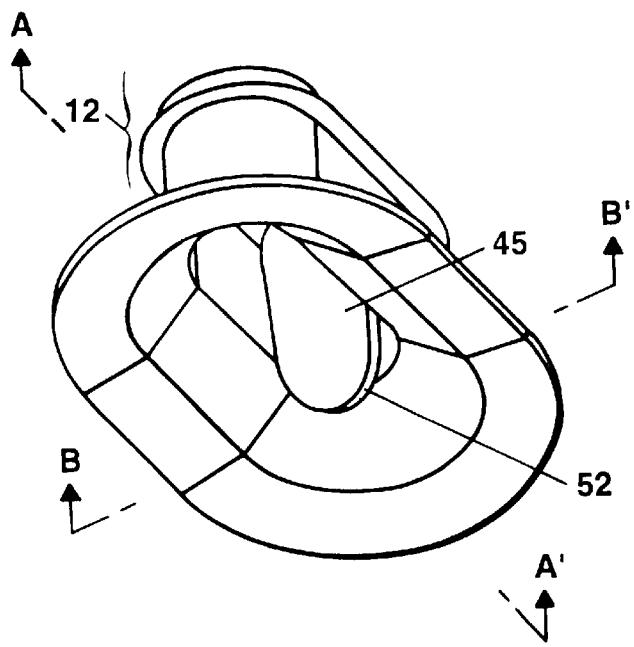
FIG. 10A is a perspective view of an embodiment of a female urinary incontinence device having an oval-shaped device body defining a cavity and a urethra obstructing member shaped as a substantially flat sheet and positioned within the cavity.
Figure 10B:
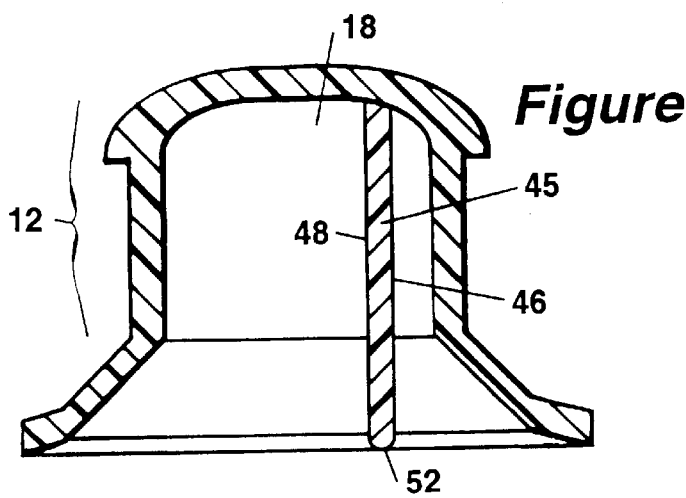
FIG. 10B is a cross-sectional view of the device of FIG. 10A taken through line A-A' of FIG. 10A.
Figure 10D:
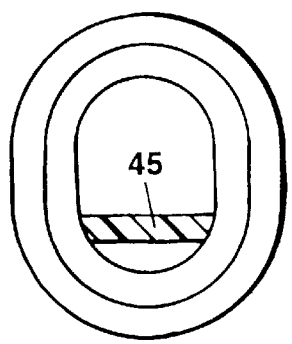
FIG. 10D is a bottom view of the device of FIG. 10A.
Figure 10C:
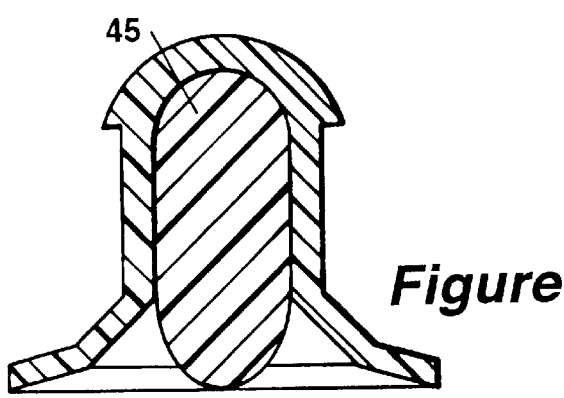
FIG. 10C is a cross-sectional view of the device of FIG. 10A taken through line B-B' of FIG. 10A.

FIGS. 9A–9C show another embodiment of the urethra obstructing member 39 having two substantially linear portions 40 and 42 respectively, and a substantially spherical pressure application member 44 attached to the substantially linear portions 40 and 42. The substantially linear portions 40 and 42 are attached to the internal surface 26 of the vacuum producing portion 12. The substantially linear portions 40 and 42 may be attached at any angle that causes the pressure application member 44 to render sufficient pressure against the user's distal urethra to adequately obstruct the urethra and alleviate urinary incontinence. In other embodiments, the pressure application member 44 is integral with linear portions 40 and 42. The pressure application member 44 may be any size or shape that renders sufficient pressure against the user's distal urethra to adequately obstruct the urethra. The pressure application member 44 may also be attached to the urethra obstructing members shown in FIGS. 2A–13C.

FIGS. 10A–10D show the urethra obstructing member 45 as a substantially flat sheet positioned within and extending across the device body's cavity 18. The urethra obstructing member 45 is positioned in the center of the cavity and substantially coplanar with the minor axis of the elliptical vacuum producing portion 12. The urethra obstructing member 45 has two substantially flat surfaces 46 and 48 respectively and a pressure applying side 52. The pressure applying side 52 extends from the vacuum producing portion 12 to apply pressure to the distal urethra and obstruct the urethra. In one embodiment, the pressure applying side 52 protrudes from the vacuum producing portion 12 a distance preferably in the range of ⅛ inch to ½ inch with ⅛ inch being preferred. As shown in FIGS. 10A–10D, the pressure applying side 52 is semicircular in shape and has a flat surface. In other embodiments, pressure applying side 52 may be linear, parabolic or any other shape designed to apply sufficient pressure against the distal urethra to substantially obstruct the urethra. In yet other embodiments, the surface of the pressure applying side 52 may be curved in shape. In still other embodiments, urethra obstructing member 45 may extend only part of the way across the device body's cavity 18.

Figure 11A:
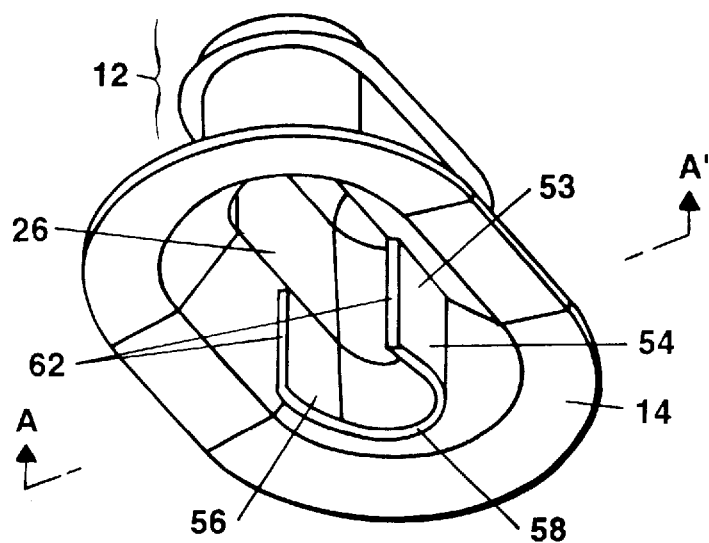
FIG. 11A is a perspective view of an embodiment of a female urinary incontinence device having an oval-shaped device body defining a cavity and a semicircular urethra obstructing member attached to and extending from the internal surface of the device body.
Figure 11B:
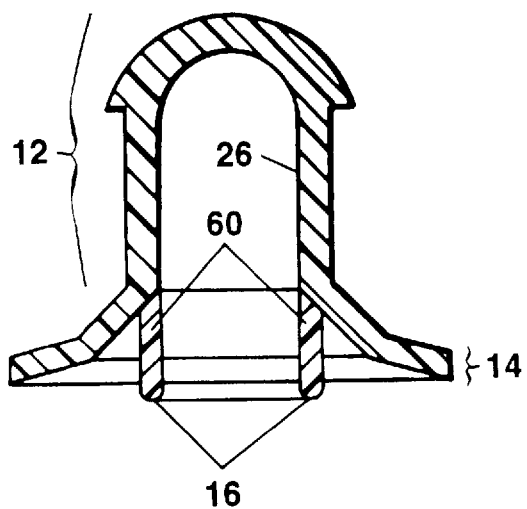
FIG. 11B is a cross-sectional view of the device of FIG. 11A taken through line A-A' of FIG. 11A.
Figure 11C:
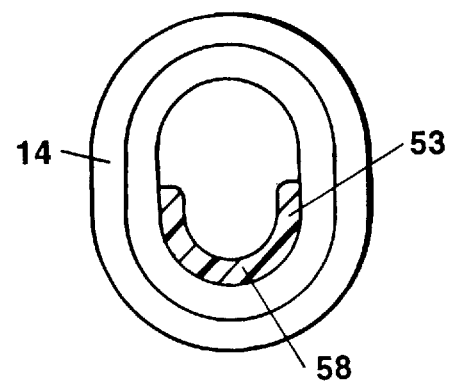
FIG. 11C is a bottom view of the device of FIG. 11A.

FIGS. 11A–11C show another embodiment of the urethra obstructing member 53 having two semicircular surfaces 54 and 56 respectively, a pressure applying surface 58, a device body contacting surface 60, and two end surfaces 62. Device body contacting surface 60 is attached to the internal surface 26 of the vacuum producing portion 12. Pressure applying surface 58 protrudes past the plane of the body contacting portion 14 to press against the distal urethra and substantially obstruct the urethra. As shown in FIGS. 11A–11C, in one embodiment, pressure applying surface 58 is flat, however it may also be rounded. Also, in other embodiments, semicircular surface 54 of urethra obstructing member 53 may be attached along the internal surface 26 of the vacuum producing portion 12 instead of the device body contacting surface 60. FIGS. 11A–11C show an embodiment of the urethra obstructing member 53 having a concave semicircular surface 56. In other embodiments, semicircular surface 56 is convex. FIGS. 11A–11C show semicircular surfaces 54 and 56 as extending one-half of the distance around the perimeter of the vacuum producing portion 12. In other embodiments, semicircular surfaces 54 and 56 may extend around the complete perimeter of vacuum producing portion 12 or any portion thereof.

Figure 12A:
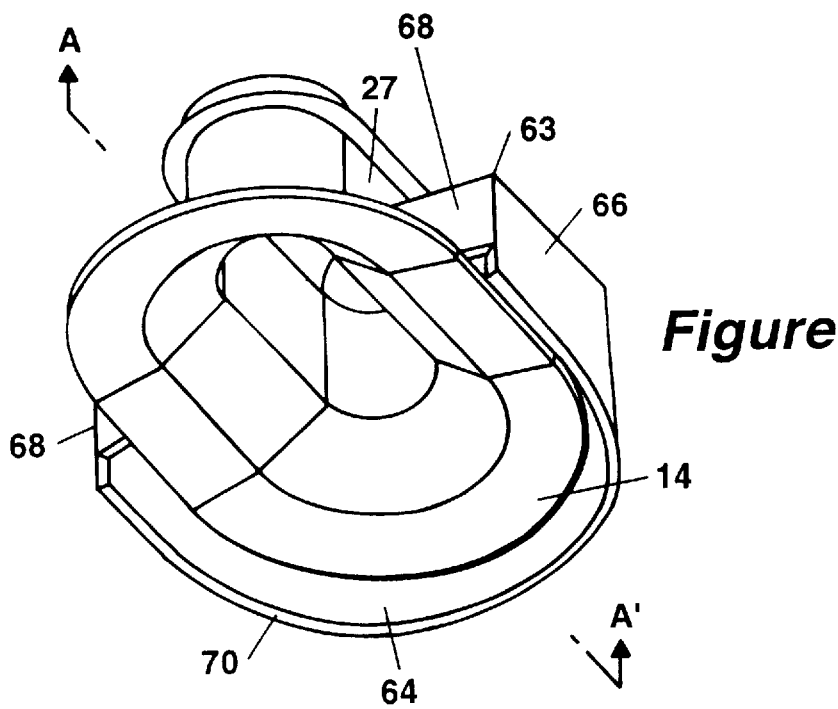
FIG. 12A is a perspective view of an embodiment of a female urinary incontinence device having an oval-shaped device body defining a cavity and a semicircular urethra obstructing member attached to the external surface of the device body.
Figure 12B:
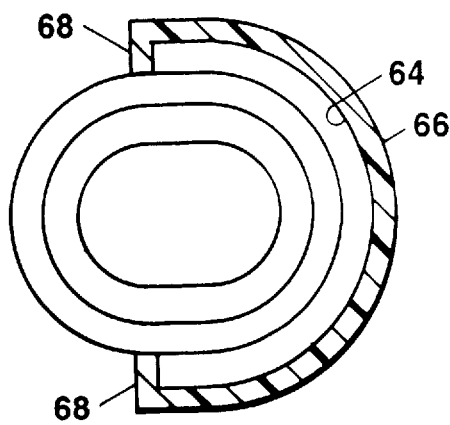
FIG. 12B is a bottom view of the device of FIG. 12A.
Figure 12C:
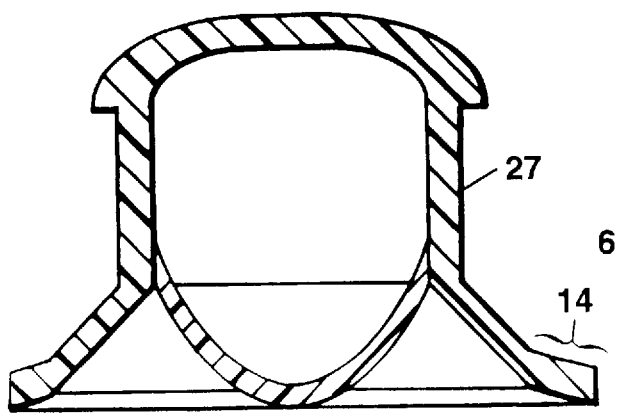
FIG. 12C is a cross-sectional view of the device of FIG. 12A taken through line A-A' of FIG. 12A.
Figure 12C:

FIGS. 12A–12C show urethra obstructing member 63 having an internal semicircular surface 64, an external semicircular surface 66, end walls 68, and a pressure applying surface 70. In one embodiment urethra obstructing member 63 has a thickness of approximately ⅛ inch. In another embodiment, internal semicircular surface 64 and external semicircular surface 66 of urethra obstructing member 63 have a height of approximately 1.0 inch and extend vertically beyond the plane of the body contacting portion 14 a distance of approximately ¼ inch. End walls 68 are attached to the external surface 27 of the vacuum producing portion 12. In one embodiment the end walls 68 extend out from the vacuum producing portion 12 a distance of approximately ⅝ inch and extend out horizontally from the edge of the body contacting portion 14 a distance of approximately ⅛ inch. In another embodiment, end walls 68 are attached to the center of the substantial vertical side walls 20 and urethra obstructing member 63 extends one-half of the distance around the perimeter of vacuum producing portion 12. In other embodiments, urethra obstructing member 63 may extend around the complete perimeter of vacuum producing portion 12 or any portion thereof.

FIGS. 13A–13C show the urethra obstructing member 70 as a lever extending through the device body's cavity 18. In one embodiment the lever has a length of approximately 2.0 inches. The urethra obstructing member 70 extends through the device body's cavity 18 through opening 72. Opening 72 is sealed with a rigid plastic. When positioning the embodiment of the device 10 shown in FIGS. 13A–13C on the user's body, the user pulls upwards on end 74 of the urethra obstructing member 70 causing end 76 of the urethra obstructing member 70 to press on the user's distal urethra.

Figure 14A:
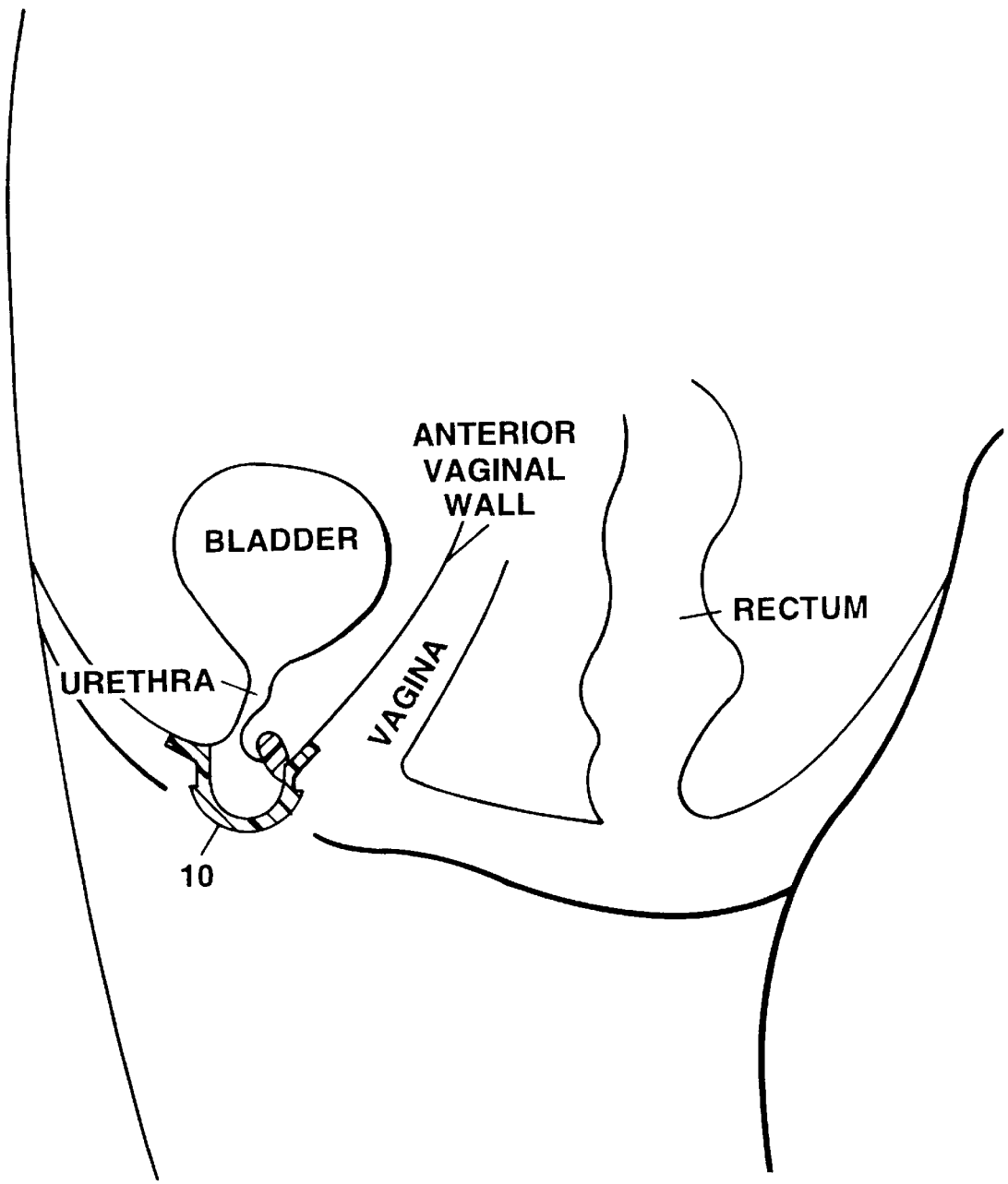
FIG. 14A is a cross-sectional view taken through line A-A' of FIG. 2A of the device of FIG. 2A when in place over the orifice of the user's urethra.
Figure 14B:
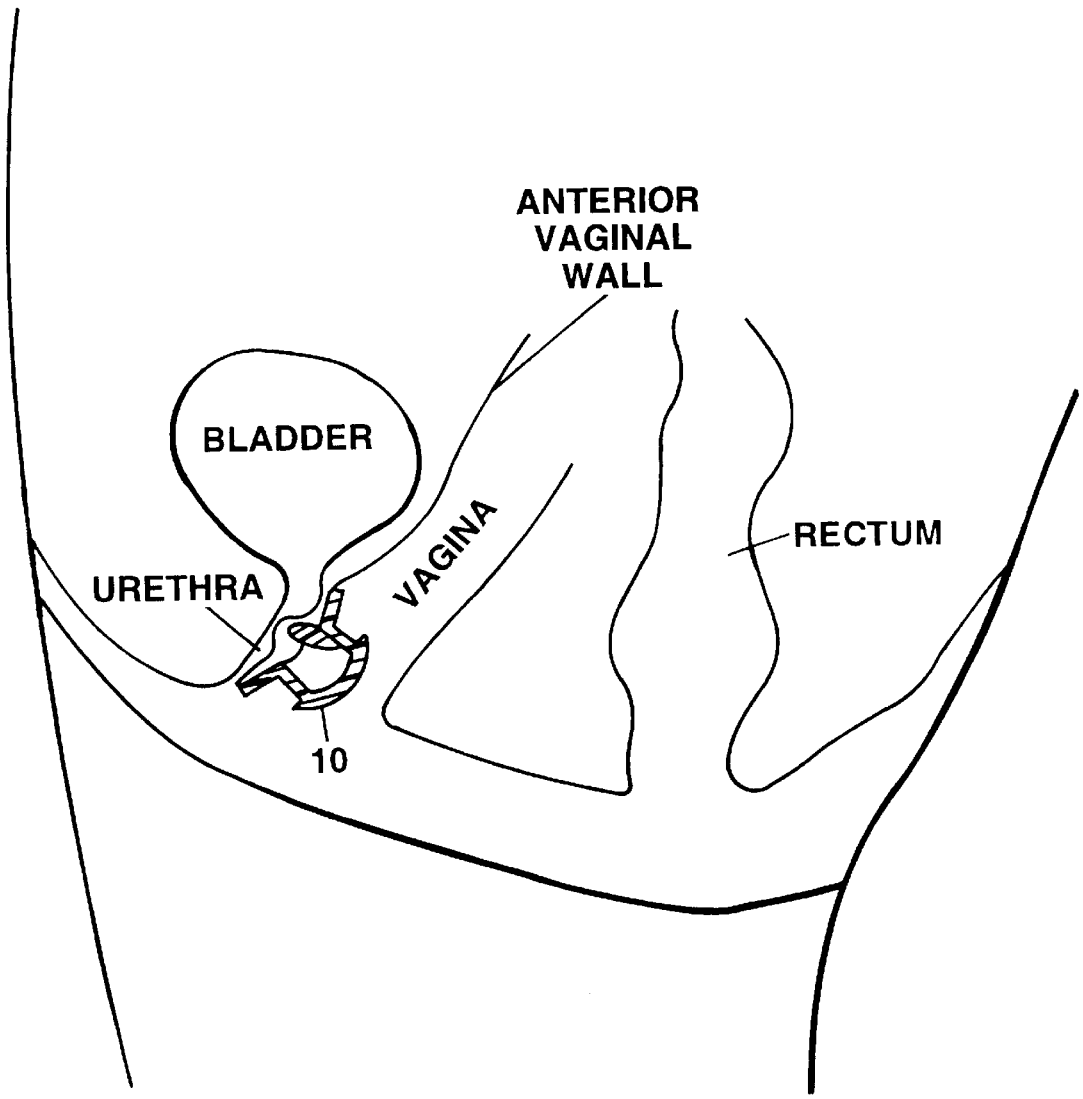
FIG. 14B is a cross-sectional view taken through line A-A' of FIG. 2A of the device of FIG. 2A when in place on the user's anterior vaginal wall along the path of the urethra.
Figure 15A:
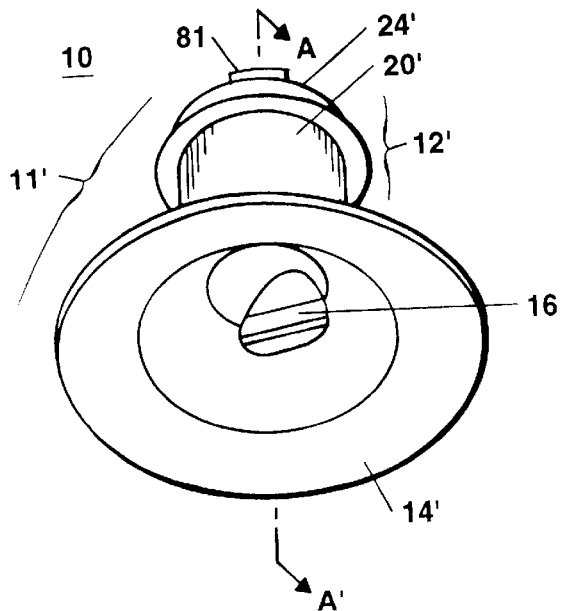
FIG. 15A is a perspective view of an embodiment of a female urinary incontinence device having a circular device body defining a cavity, an aperture in the ceiling of the device body, a membrane covering the aperture and a urethra obstructing member attached to and extending from the device body.
Figure 15C:
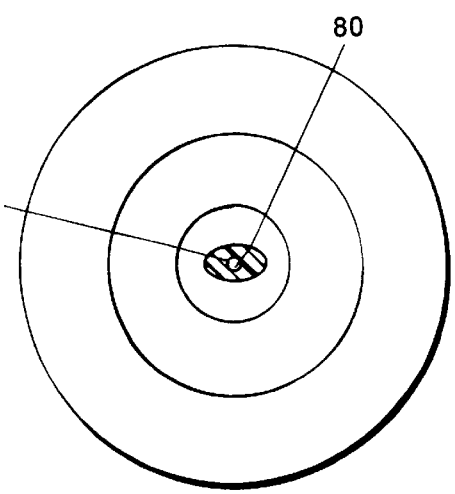
FIG. 15C is a top view of the device of FIG. 15A.
Figure 15B:
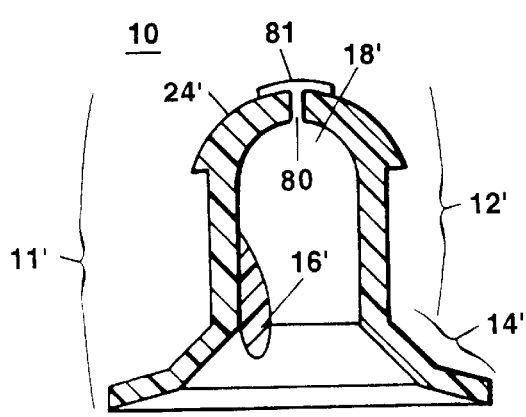
FIG. 15B is a cross-sectional view of the device of FIG. 15A taken through line A-A' of FIG. 15A.
Figure 15D:
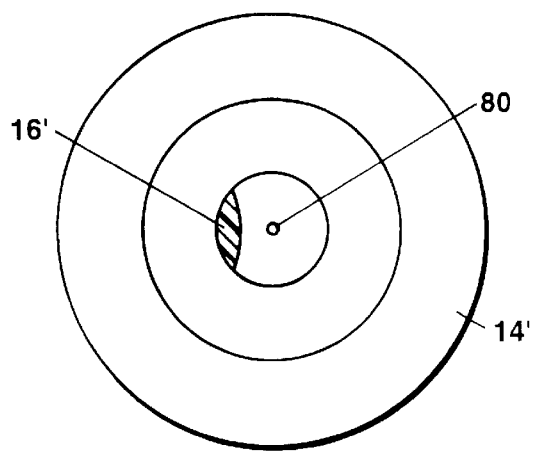
FIG. 15D is a bottom view of the device of FIG. 15A.

FIGS. 14A and 14B show the female urinary incontinence device of FIG. 2A in use. Using a female urinary incontinence device 10 made of a resilient and partially flexible material is accomplished in the following manner. The user inwardly compresses the vacuum producing portion 12. The user then positions the body contacting portion 14 of device 10 over the user's body and applies the body contacting portion 14 to the user's body. In the embodiment shown in FIG. 14A, the user positions the body contacting portion 14 over the meatus urinarius and applies the body contacting portion 14 to the area surrounding the meatus. In the preferred state, the urethra obstructing member 16 is pointed downward and toward the anterior vagina. In the embodiment shown in FIG. 14B, the user positions the body contacting portion 14 over the anterior vaginal wall along the path of the urethra and applies the body contacting portion 14 to the anterior vaginal wall. The user then releases the vacuum producing portion 12. At this point, because it is made of a resilient material, the device body 11 will expand towards its original shape creating a vacuum within the device body's cavity 18. The vacuum causes the outside atmospheric pressure to press against the body contacting portion 14 and hold the device 10 onto the user's body. Once the device 10 is in place, the urethra obstructing member 16 presses against and deforms the user's distal urethra causing the urethra to be substantially obstructed, thereby alleviating urinary incontinence. When the user wishes to remove the device 10, the user releases the vacuum in the device body's cavity 18 and removes the body contacting portion 14 from the area surrounding the meatus or the anterior vaginal wall. The user may release the vacuum by compressing the device body 11 or by breaking the seal between the device body 11 and the tissue.

In the embodiment shown in FIG. 14A, when the device 10 is positioned over the user's meatus, the urethra obstructing member 16 works in conjunction with the body contacting portion 14 to alleviate urinary incontinence. While the urethra obstructing member 16 presses against the distal urethra to obstruct the urethra, the body contacting portion 14 gently compresses the area surrounding the user's meatus to close the meatus to urine flow. In the embodiment shown in FIG. 14B, the body contacting portion 14 does not aid in closing the meatus, but rather the device relies completely on the urethra obstructing member 16 to obstruct the urethra and alleviate urinary incontinence.

In order to reduce the danger of infection, the device may be made to be non-reusable or of limited re-use. This limitation may be achieved by fabricating the device of a material which will permit a limited number of compressions prior to deteriorating. Such materials may include thermoplastic elastomers and urethanes. Alternatively, the device may be constructed to include physical barriers to re-use.

FIGS. 15A–22C show non-reusable and limited re-use embodiments of the female urinary incontinence device described above and shown in FIGS. 3A–3C. The remainder of the embodiments described above may also be modified to incorporate the non-reusable and limited re-use features shown in FIGS. 15A–22C. FIGS. 15A–15D show the female urinary incontinence device of FIGS. 3A–3C having an aperture 80 in the ceiling 24' of the device body 11' and a removable membrane 81 covering the aperture 80. The removable membrane 81 is sized to completely cover the aperture 80. The removable membrane 81 may be made of any rigid or resilient material that is sufficient to maintain the vacuum formed within the device body's cavity 18'. In preferred embodiments, the removable membrane is composed of FDA approved silicone rubber, urethane or thermoplastic elastomers and is removably attached to the device body with an adhesive. After use, the user may release the vacuum in the device body's cavity 18' by removing the membrane 81. Removing the membrane 81 creates a communication between the device body's cavity 18' and the exterior of the device 10 through the aperture 80. Removing the membrane 81 allows air from the exterior of the device 10 to enter the device body's cavity 18' through the aperture 80. In other embodiments, the aperture 80 and membrane 81 may be located at any position on the vacuum producing portion 12'. Although the embodiment is shown in conjunction with a female urinary incontinence device having a urethra obstructing member, the non-reusable or limited re-use feature is also usable in incontinence devices without a urethra obstructing member.

Figure 16A:
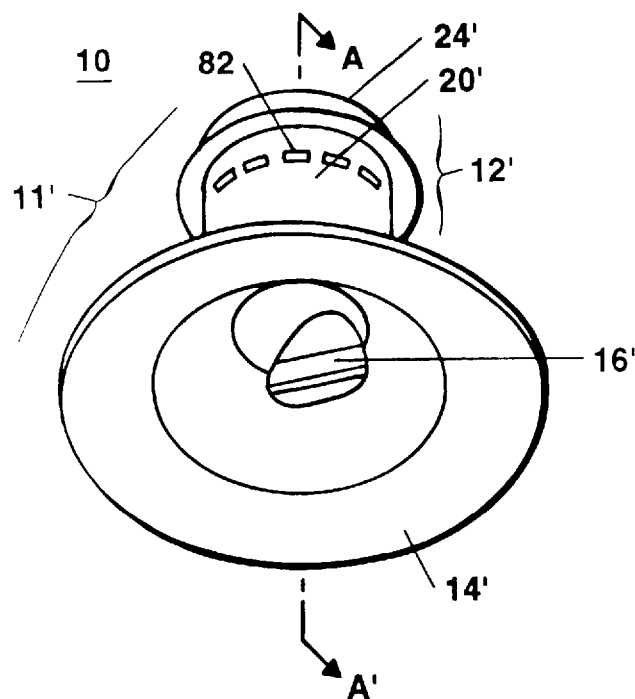
FIG. 16A is a perspective view of an embodiment of a female urinary incontinence device having a circular device body defining a cavity, perforations surrounding the top portion of the device body and a urethra obstructing member attached to and extending from the device body.
Figure 16B:
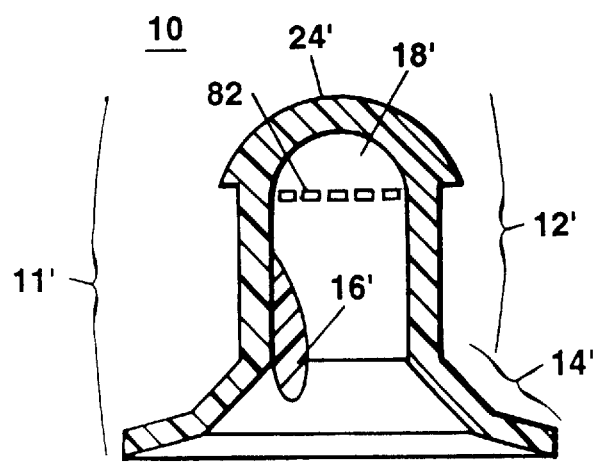
FIG. 16B is a cross-sectional view of the device of FIG. 16A taken through line A-A' of FIG. 16A.

FIGS. 16A–16B show another non-reusable or limited re-use embodiment of the female urinary incontinence device described above and shown in FIGS. 3A–3C. FIGS. 16A–16B show the device of FIGS. 3A–3C having perforations 82 surrounding the vacuum producing portion 12'. The perforations 82 surround the vacuum producing portion 12' at any location along the vertical wall 20'. After use, the user may release the vacuum in the device body's cavity 18' by tearing away the ceiling 24' or a portion of the device body 11'. Tearing away a portion of the device creates a communication between the device body's cavity 18' and the exterior of the device 10. Removing portion of the device allows air from the exterior of the device 10 to enter the device body's cavity 18' and destroy the vacuum within the device body's cavity 18'. The perforations 82 may be of any size or shape that maintains the vacuum within the device body's cavity 18' while the device 10 is in use and allows a user to release the vacuum within the device body's cavity 18' without pulling the entire device off of the user's body. Although the embodiment is shown in conjunction with a female urinary incontinence device having a urethra obstructing member, the non-reusable or limited reuse feature is also usable in incontinence devices without a urethra obstructing member.

Figure 17A:
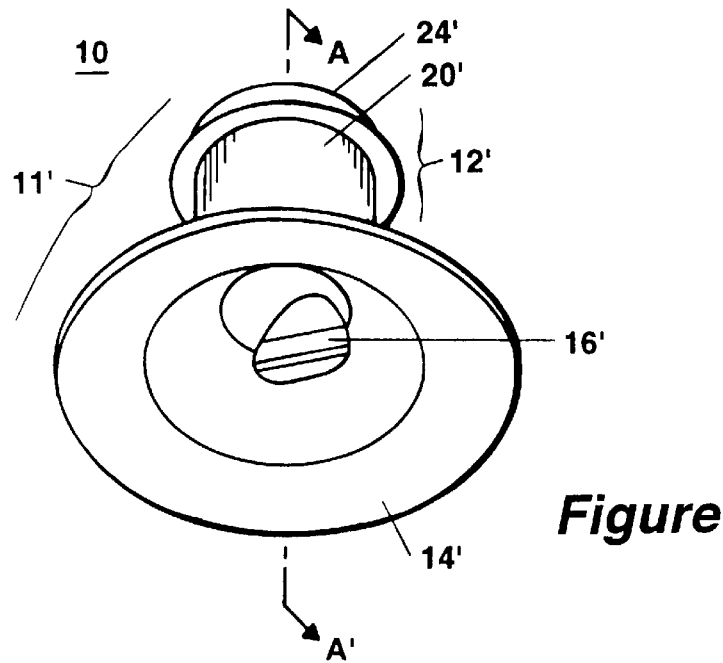
FIG. 17A is a perspective view of an embodiment of a female urinary incontinence device having a circular device body defining a cavity, two hook-shaped interlocking members attached to and extending toward the center of the device body and a urethra obstructing member attached to and extending from the device body.
Figure 17B:
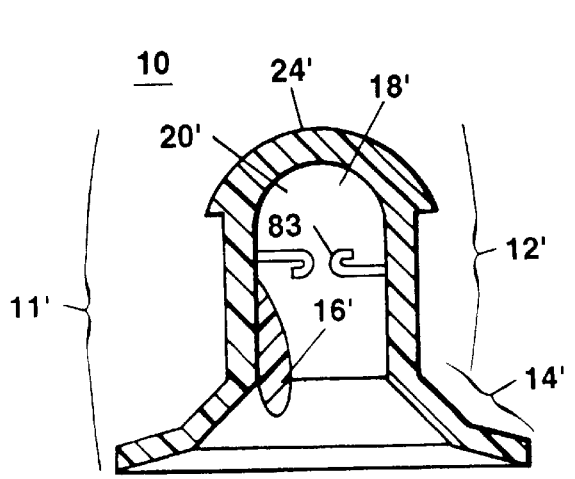
FIG. 17B is a cross-sectional view of the device of FIG. 17A taken through line A-A' of FIG. 17A.
Figure 17C:
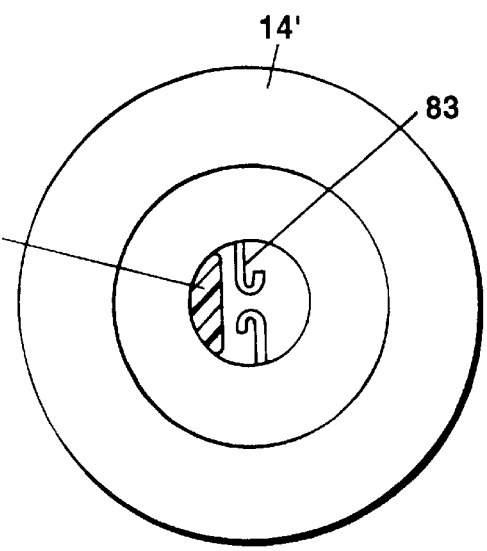
FIG. 17C is a bottom view of the device of FIG. 17A.

FIGS. 17A–17C show the urinary incontinence device 10 of FIGS. 3A–3C having two interlocking members 83 attached to and extending from the substantially vertical wall 20'. The interlocking members 83 are hook-shaped and extend toward the center of the device body's cavity 18'. Upon at least partial compression of the device body 11', the two hook-shaped interlocking members 83 engage and interlock. Once interlocked, the interlocking members 83 prevent complete re-expansion of the device body 11', thereby causing the device to be non-reusable. Although the embodiment is shown in conjunction with a female urinary incontinence device having a urethra obstructing member, the non-reusable or limited re-use feature is also usable in incontinence devices without a urethra obstructing member.

Figure 18A:
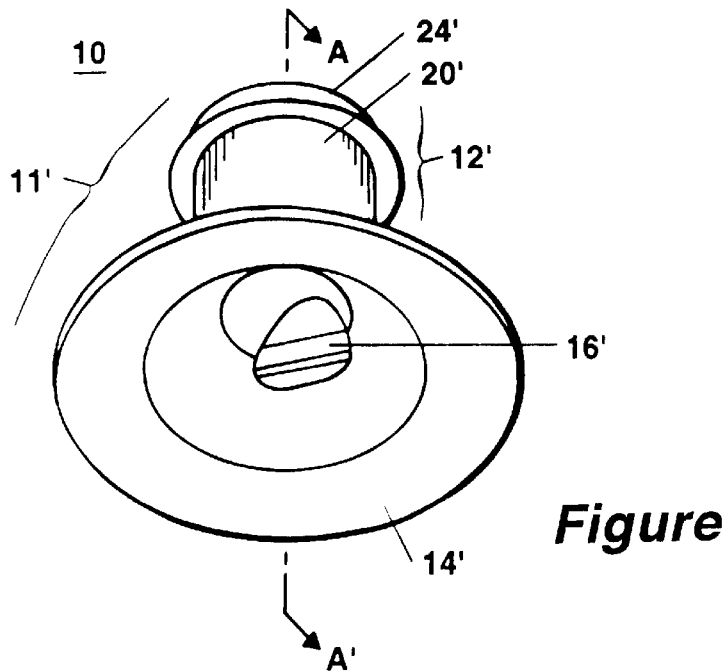
FIG. 18A is a perspective view of an embodiment of a female urinary incontinence device having a circular device body defining a cavity, two interlocking members having notched edges attached to and extending toward the center of the device body and a urethra obstructing member attached to and extending from the device body.
Figure 18B:
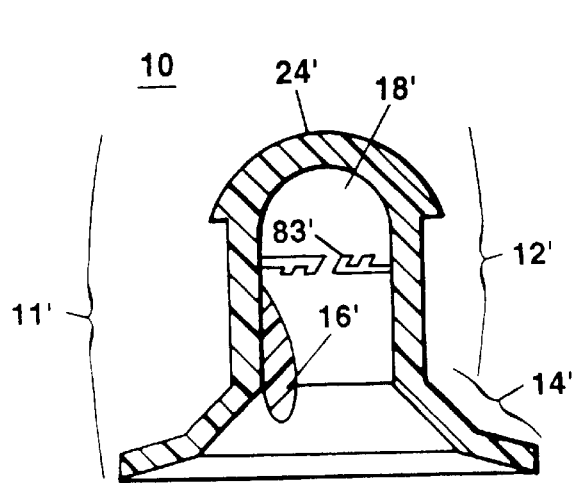
FIG. 18B is a cross-sectional view of the device of FIG. 18A taken through line A-A' of FIG. 18A.
Figure 18C:
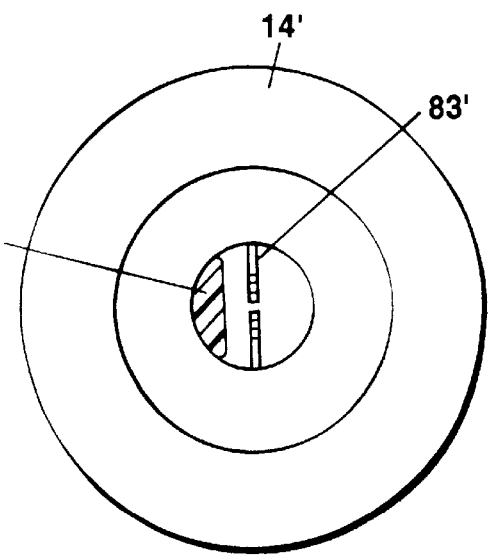
FIG. 18C is a bottom view of the device of FIG. 18A.
Figure 19A:
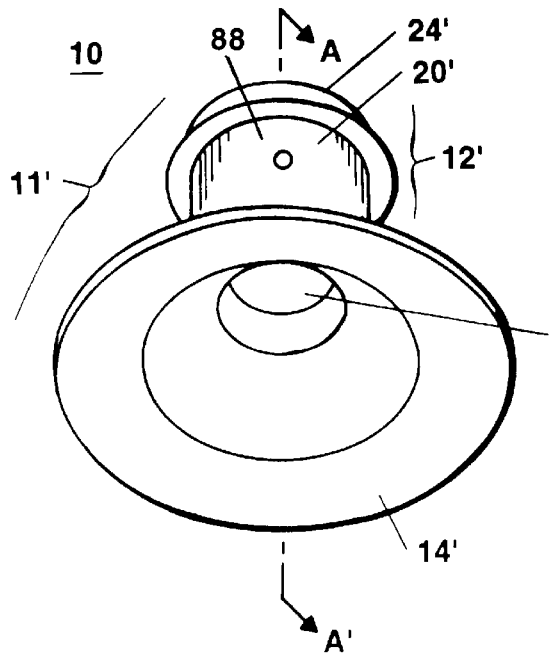
FIG. 19A is a perspective view of an embodiment of a female urinary incontinence device having a circular device body defining a cavity, an aperture in the side wall of the device body, a membrane attached to the external surface of the device body and covering the aperture, two hook-shaped interlocking members extending toward the center of the device body, and a urethra obstructing member attached to and extending from the device body.
Figure 19B:
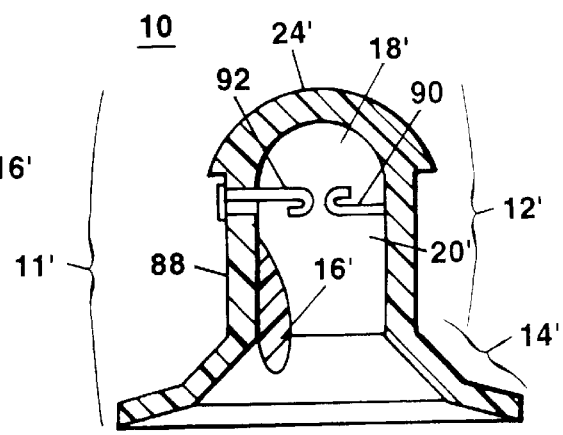
FIG. 19B is a cross-sectional view of the device of FIG. 19A taken through line A-A' of FIG. 19A.
Figure 19C:
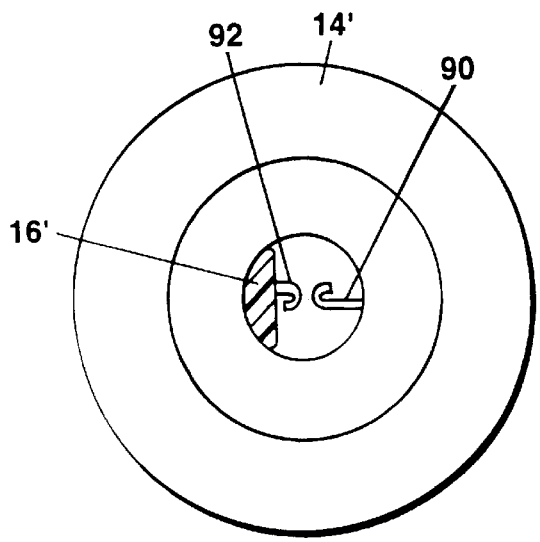
FIG. 19C is a bottom view of the device of FIG. 19A.
Figure 19D:
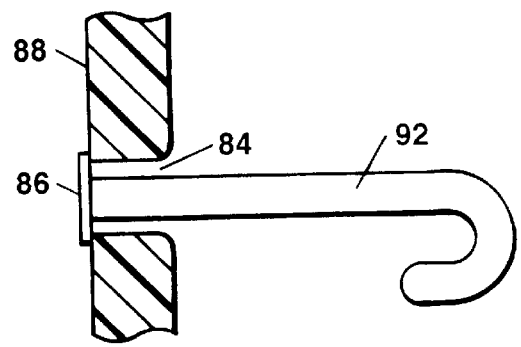
FIG. 19D is a detailed view of a portion of FIG. 19B showing the aperture, the membrane covering the aperture and the hook-shaped interlocking member extending through the aperture and being attached to the membrane.
Figure 20A:
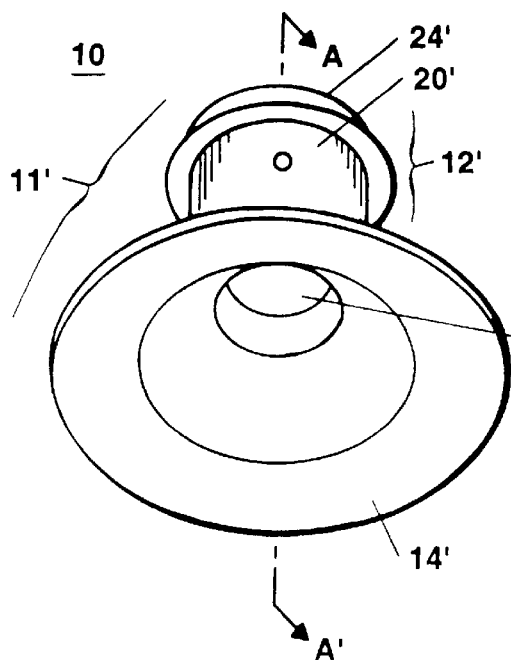
FIG. 20A is a perspective view of an embodiment of a female urinary incontinence device having a circular device body defining a cavity, an aperture in the side wall of the device body, a membrane attached to the internal surface of the device body and covering the aperture, two hook-shaped interlocking members extending toward the center of the device body, and a urethra obstructing member attached to and extending from the device body.
Figure 20B:
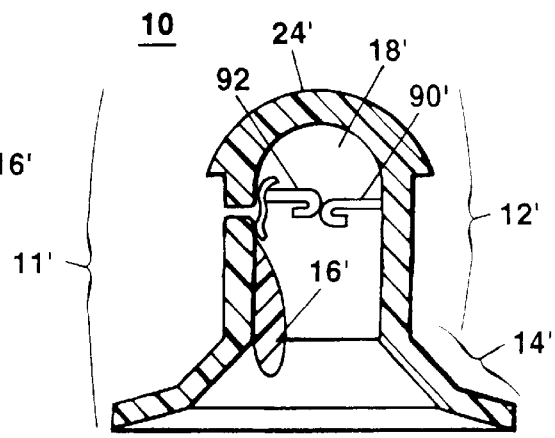
FIG. 20B is a cross-sectional view of the device of FIG. 20A taken through line A-A' of FIG. 20A.
Figure 20C:
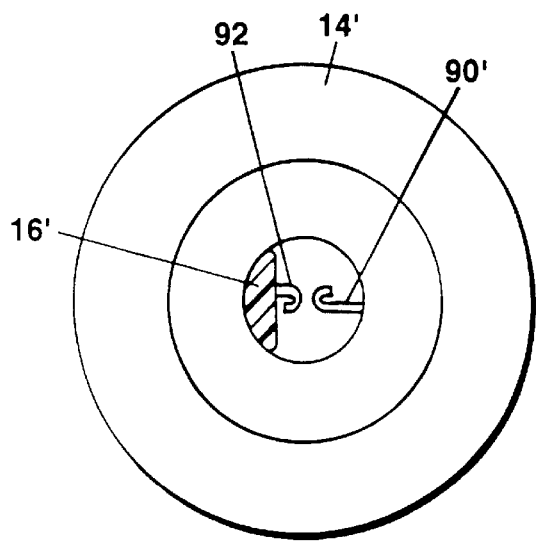
FIG. 20C is a bottom view of the device of FIG. 20A.
Figure 20D:
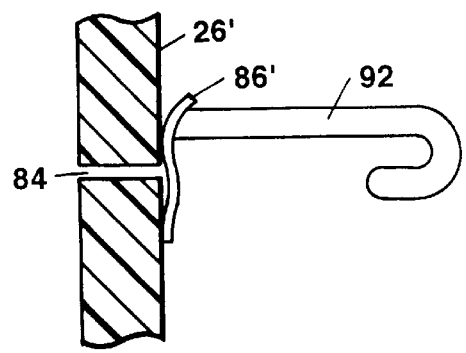
FIG. 20D is a detailed view of a portion of FIG. 20B showing the aperture, the membrane covering the aperture and the hook-shaped interlocking member attached to the membrane.
Figure 21A:
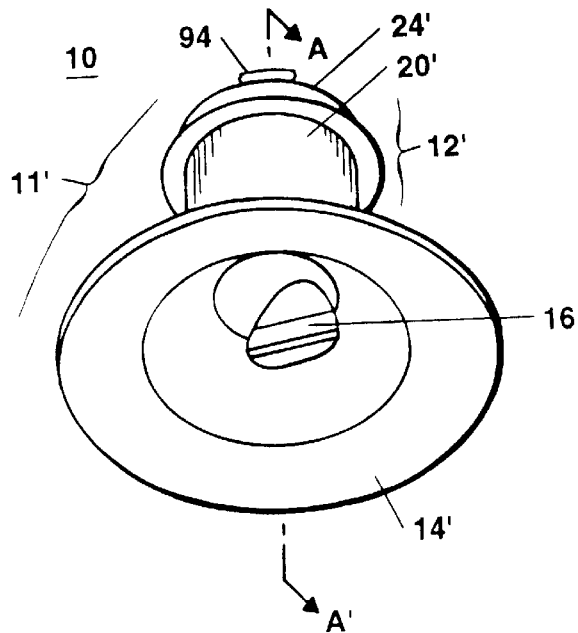
FIG. 21A is a perspective view of an embodiment of a female urinary incontinence device having a circular device body defining a cavity, an aperture in the ceiling of the device body and a water soluble plug within the aperture.
Figure 21C:
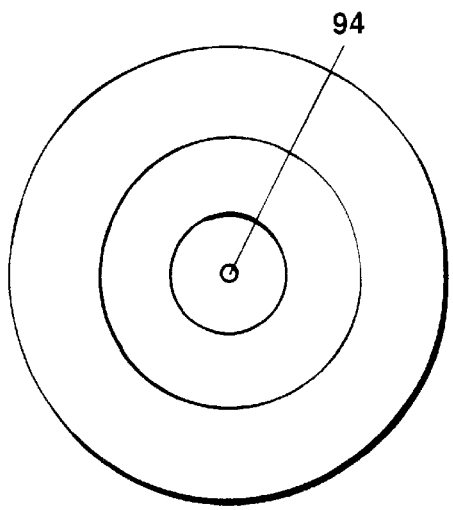
FIG. 21C is a top view of the device of FIG. 21A.
Figure 21B:
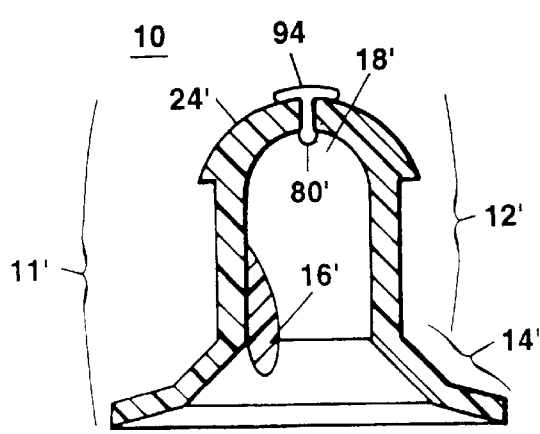
FIG. 21B is a cross-sectional view of the device of FIG. 21A taken through line A-A' of FIG. 21A.
Figure 21D:
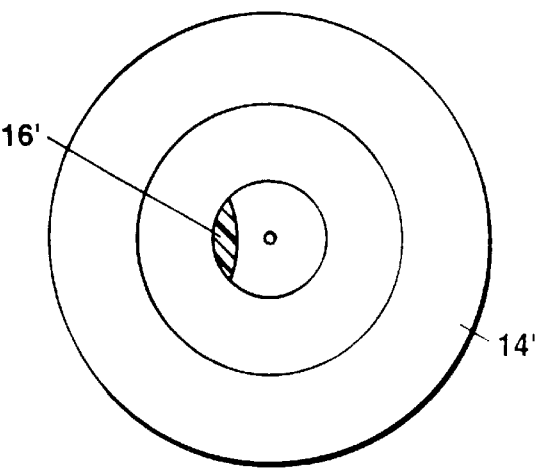
FIG. 21D is a bottom view of the device of FIG. 21A.

FIGS. 18A–18C show the interlocking members 83' having notched edges. Similar to the device described above and shown in FIGS. 17A–17C, the interlocking members 83' engage and interlock upon at least partial compression of the device body 11'. Once engaged, the interlocking members 83' prevent complete re-expansion of the device body 11', thereby causing the device to be non-reusable. The interlocking members 83 may be any other shape so long as the members engage and interlock upon at least partial compression of the device body 11' and prevent complete re-expansion of the device body 11' once engaged. Although the embodiment is shown in conjunction with a female urinary incontinence device having a urethra obstructing member, the non-reusable or limited re-use feature is also usable in incontinence devices without a urethra obstructing member.

FIGS. 19A–19D show the urinary incontinence device 10 of FIGS. 3A–3C having an aperture 84 in the substantially vertical wall 20', a membrane 86 attached to the external surface 88 of the device body 11', and two interlocking members 90 and 92, respectively. The membrane 86 is sized and shaped to completely cover the aperture 84. The two interlocking members 90, 92 are hook-shaped and extend toward the center of the device body's cavity 18'. Interlocking member 90 is attached to and extends from the internal surface of the substantially vertical wall 20'. Interlocking member 92 extends through the aperture 84 and is attached to the membrane 86. Upon at least partial compression of the device body 11', the two hook-shaped interlocking members 90, 92 engage and interlock. Upon re-expansion of the device body 11', the interlocking members 90, 92 detach at least a portion of the removable membrane 86, thereby allowing air from the exterior of the device 10 to enter the device body's cavity 18' through the aperture 84. Opening the aperture 84 destroys the vacuum within the device body's cavity 18', thereby making the device non-reusable. The two interlocking members 90, 92 may be any other shape so long as the members engage upon at least partial compression of the device body 11' and detach at least a portion of the removable membrane 86 upon re-expansion of the device body 11'. Although the embodiment is shown in conjunction with a female urinary incontinence device having a urethra obstructing member, the non-reusable or limited re-use feature is also usable in incontinence devices without a urethra obstructing member.

FIGS. 20A–20D show the membrane 86' attached to the internal surface 26' of the vacuum producing portion 12'. Although the embodiment is shown in conjunction with a female urinary incontinence device having a urethra obstructing member, the non-reusable or limited re-use feature is also usable in incontinence devices without a urethra obstructing member.

FIGS. 21A–21D show another non-reusable or limited re-use embodiment of the female urinary incontinence device described above and shown in FIGS. 3A–3C. FIGS. 21A–21D show the device of FIGS. 3A–3C having an aperture 80' in the ceiling 24' of the device body 11' and a water soluble plug 94 within the aperture 80'. In one embodiment, the water soluble plug 94 is composed of a polymer material. The water soluble plug may be composed of polyvinyl alcohol, polyvinyl paredone or methylhydroxypropyl cellulose. The water soluble plug 94 may also be composed of any other material which dissolves upon contact with water. In a non-reusable embodiment, the water soluble plug 94 disintegrates quickly upon exposure to water during cleaning of the device. Once the water soluble plug 94 is substantially disintegrated, the aperture 80' is opened and the vacuum within the device body's cavity 18' destroyed. In a limited re-use embodiment, the water soluble plug 94 is composed of a material which dissolves slowly upon exposure to water during cleaning of the device. This limited re-use embodiment would require multiple contacts with water before the plug 94 disintegrates sufficiently to allow air to pass through the aperture 80'. In other embodiments, the aperture 80' and plug 94 may be located at any position on the vacuum producing portion 12'. Although the embodiment is shown in conjunction with a female urinary incontinence device having a urethra obstructing member, the non-reusable or limited re-use feature is also usable in incontinence devices without a urethra obstructing member.

Figure 22A:
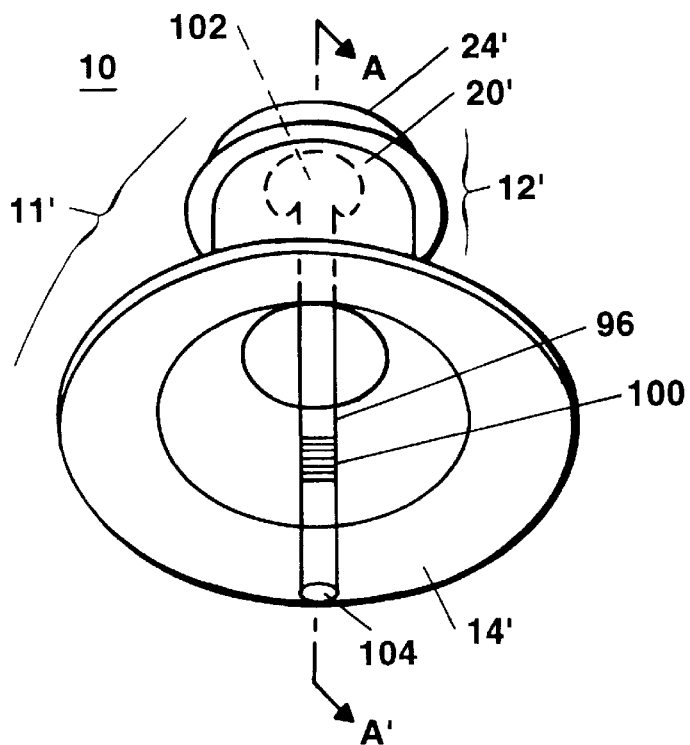
FIG. 22A is a perspective view of an embodiment of a female urinary incontinence device having a circular device body defining a cavity, a channel within the side wall of the device body, a valve mechanism located within the channel and a balloon apparatus connected to the channel.
Figure 22C:
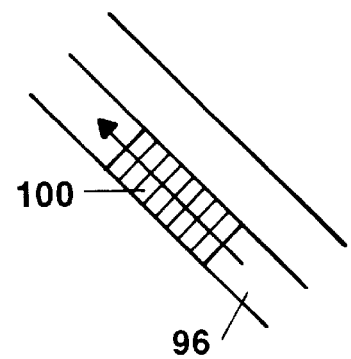
FIG. 22C is a detailed view of a portion of FIG. 22B showing the valve within the side wall of the device body.
Figure 22B:
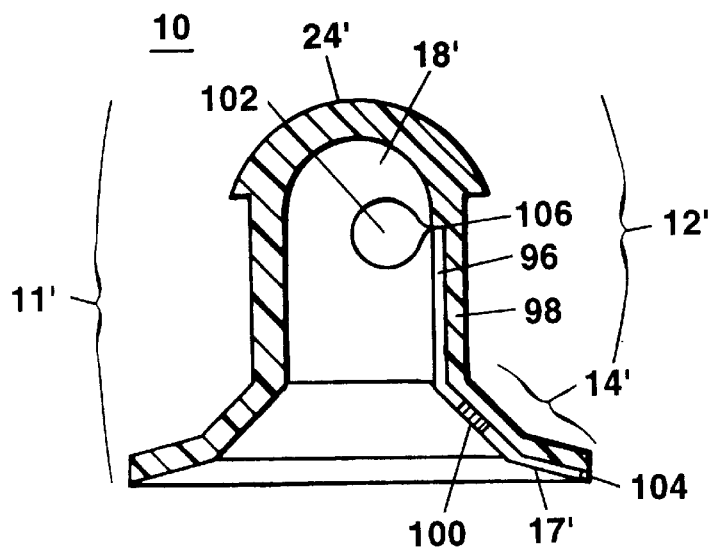
FIG. 22B is a cross-sectional view of the device of FIG. 22A taken through line A-A' of FIG. 22A.

FIGS. 22A–22C show another non-reusable or limited re-use embodiment of the female urinary incontinence device described above and shown in FIGS. 3A–3C without the urethra obstructing member. FIGS. 22A–22C show the device of FIGS. 3A–3C having a channel 96 within the side wall 98 of the device body 11', a valve mechanism 100 located within the channel 96 and an inflatable balloon apparatus 102 connected to the channel. In one embodiment, the channel 96 has a first opening 104 at the edge of the rim 17'. In other embodiments, the opening 104 may be located at other positions along the device body 11'. In the embodiment shown in FIGS. 22A–22B, the channel 96 extends along the body contacting portion 14' and a portion of the vacuum producing portion 12'. The channel 96 has a second opening 106 which connects the channel 96 to the balloon apparatus 102 residing within the device body 11'. The valve mechanism 100 is located within the channel 96. In one embodiment, the valve mechanism 100 is a one-way air valve which permits unidirectional air flow through the channel 96 and into the balloon apparatus 102. To apply the device, the user compresses the vacuum producing portion 12', positions the device on the user's body, and then releases the vacuum producing portion 12'. Upon release, the vacuum producing portion 12' expands toward its original shape. Upon expansion of the vacuum producing portion 12', air enters the channel 96 through opening 104, passes through the channel 96 and into the balloon apparatus 102, thereby inflating the balloon apparatus 102. Because the valve mechanism 100 only permits unidirectional air flow, the air is trapped in the balloon apparatus 102. Once inflated, the balloon apparatus 102 prevents recompression of the vacuum producing portion 12', thereby preventing re-use of the device. Although the embodiment is shown in conjunction with a female urinary incontinence device having a urethra obstructing member, the non-reusable or limited re-use feature is also usable in incontinence devices without a urethra obstructing member.

Figure 23A:
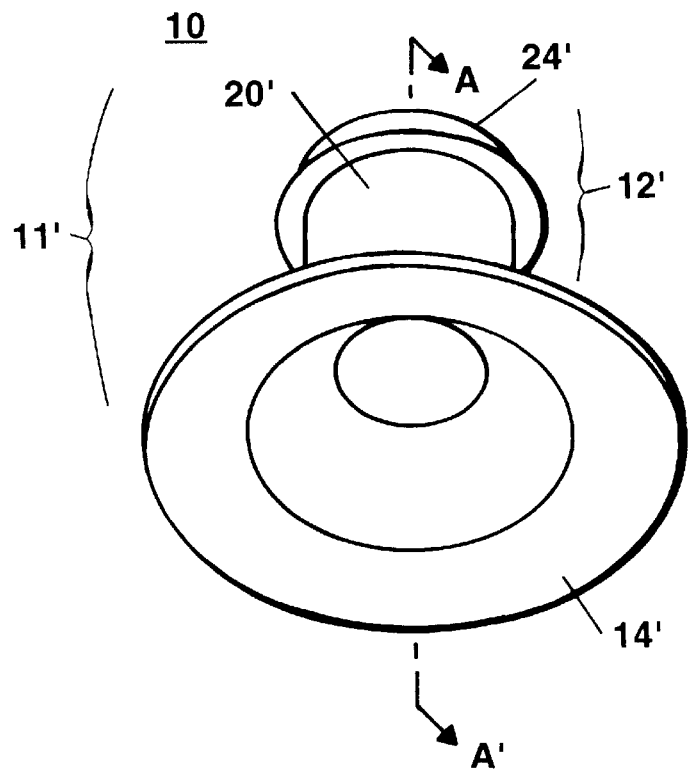
FIG. 23A is a perspective view of an embodiment of a female urinary incontinence device having a circular device body defining a cavity and two protuberances attached to and extending from the device body.
Figure 23B:
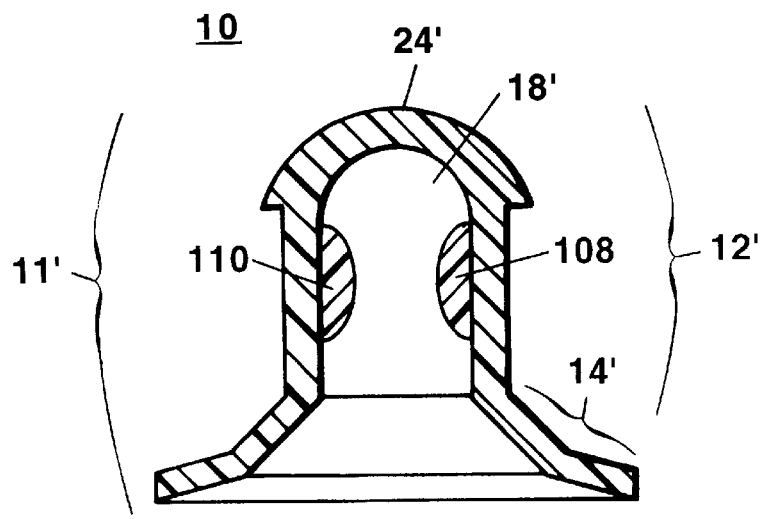
FIG. 23B is a cross-sectional view of the device of FIG. 23A taken through line A-A' of FIG. 23A.

FIGS. 23A–23B show another embodiment of a female urinary incontinence device according to the invention having a device body 11' and two protuberances 108 and 110, respectively, attached to the device body 11'. The purpose of the protuberances 108, 110 is to act as a volume limiter to regulate the amount of volume within the device body's cavity 18', and thereby regulate the amount of vacuum applied to the user's meatus. In the embodiments described above, the user is able to control the amount of vacuum applied to the user's meatus. The amount of vacuum produced by the device depends on the volume within the device body's cavity 18'. The user can vary the amount of vacuum applied to the meatus by varying the compression of the device's vacuum producing portion 12' upon placement of the device on the user's body. The embodiment shown in FIGS. 23A–23B limits the amount of vacuum the device can apply to the user's meatus. The protuberances 108, 110 extend into the device body's cavity 18'. The protuberances 108, 110 are sized, shaped and positioned to collide upon a predetermined compression of the vacuum producing portion 12'. When the user compresses the vacuum producing portion 12' by a predetermined amount, the protuberances 108, 110 collide and prevent the user from further compressing the vacuum producing portion 12'. Compressing the vacuum producing portion 12' until the protuberances collide enables the user to create approximately the same predetermined, measured amount of air displacement and vacuum during each use.

Having described preferred embodiments of the invention, it will now become apparent to one of skill in the art that other embodiments incorporating the concepts may be used. It is felt, therefore, that these embodiments should not be limited to disclosed embodiments but rather should be limited only by the spirit and scope of the following claims.

What is claimed is:

1. A female urinary incontinence device comprising:
    a resilient and at least partially flexible device body defining a cavity having an opening, said device body having an internal surface and an external surface; and
    at least one urethra obstructing member attached to said device body, said urethra obstructing member being shaped to deform the urethra of a user's body and to cause the urethra to be substantially obstructed;
    wherein when said urinary incontinence device is adapted to be positioned on the means of said user's body, at least partial compression of said device body produces a vacuum within said cavity sufficient to hold said urinary incontinence device onto said user's body.

2. The urinary incontinence device of claim 1 wherein said urethra obstructing member is shaped to cause said urethra to be completely obstructed.

3. The urinary incontinence device of claim 1 wherein said at least one urethra obstructing member is integral with said device body.

4. The urinary incontinence device of claim 1 wherein said device further comprises a body contacting portion encircling said cavity opening, said body contacting portion being adapted to contact said user's body.

5. The urinary incontinence device of claim 4 wherein said body contacting portion of said device body is circular.

6. The urinary incontinence device of claim 4 wherein said body contacting portion of said device body is oval shaped.

7. The urinary incontinence device of claim 4 wherein said body contacting portion is adapted for scaling said incontinence device to the user's body and preventing any air from entering said cavity of said device body or fluid from escaping said cavity of said device body.

8. The urinary incontinence device of claim 1 wherein said at least one urethra obstructing member is rigid.

9. The urinary incontinence device of claim 1 wherein said device body is capable of substantially closing the meatus of the user's body.

10. The urinary incontinence device of claim 1 wherein said device body is capable of completely closing the meatus of the user's body.

11. The urinary incontinence device of claim 1 wherein the urethra of the user has a distal portion and said at least one urethra obstructing member has a first end and a second end, said first end of said at least one urethra obstructing member being attached to said internal surface of said device body and said second end of said urethra obstructing member extending from said device body and being adapted to press against said distal portion of the urethra to substantially obstruct said urethra.

12. The urinary incontinence device of claim 11 wherein said second end of said urethra obstructing member extends from said device body to deform and completely obstruct the urethra.

13. The urinary incontinence device of claim 11 wherein said device body is oval-shaped, having a first semicircular end wall, a second semicircular end wall, a first substantially straight side wall, and a second substantially straight side wall, and wherein said first end of said at least one urethra obstructing member is attached to one of said first and second semicircular end walls of said device body, said urethra obstructing member extending from said one of said first and second semicircular end walls to deform and substantially obstruct said urethra.

14. The urinary incontinence device of claim 1 wherein said device body is oval-shaped, having a first semicircular end wall, a second semicircular end wall, a first substantially straight side wall and a second substantially straight side wall.

15. The urinary incontinence device of claim 1 wherein said device body is circular in shape.

16. The urinary incontinence device of claim 1 wherein said at least one urethra obstructing member has a first end and second end, said first end and said second end of said urethra obstructing member being attached to said internal surface of said device body, said at least one urethra obstructing member extending across said cavity.

17. The urinary incontinence device of claim 16 wherein said at least one urethra obstructing member is substantially linear in shape.

18. The urinary incontinence device of claim 16 wherein said at least one urethra obstructing member is substantially non-linear in shape.

19. The urinary incontinence device of claim 16 wherein said at least one urethra obstructing member further comprises:
   a substantially linear portion having a first end and second end, at least one of said first end and said second end of said substantially linear portion being attached to said internal surface of said device body; and
   a pressure application member attached to said substantially linear portion.

20. The urinary incontinence device of claim 19 wherein said pressure application member is integral with said substantially linear portion of said urethra obstructing member.

21. The urinary incontinence device of claim 19 wherein said at least one urethra obstructing member extends across said cavity.

22. The urinary incontinence device of claim 1 wherein said device body has a substantially minor axis, and wherein said at least one urethra obstructing member is a substantially flat sheet positioned within said cavity and substantially coplanar with said minor axis of said device body, said flat sheet having a pressure applying side extending from said urinary incontinence device to deform said urethra.

23. The urinary incontinence device of claim 22 wherein said pressure applying side of said urethra obstructing member is substantially linear in shape.

24. The urinary incontinence device of claim 22 wherein said pressure applying side of said urethra obstructing member is substantially non-linear in shape.

25. The urinary incontinence device of claim 22 wherein said at least one urethra obstructing member extends across said cavity.

26. The urinary incontinence device of claim 1 wherein said at least one urethra obstructing member has at least one semicircular surface having a first edge and a second edge.

27. The urinary incontinence device of claim 26 wherein one of said at least one semicircular surface of said urethra obstructing member is attached to said internal surface of said device body.

28. The urinary incontinence device of claim 26 wherein said first edge and said second edge of said at least one semicircular surface are attached to said external surface of said device body.

29. The urinary incontinence device of claim 1 wherein said device body and said urethra obstructing member are composed of two different grades of silicone rubber having different stiffness.

30. The urinary incontinence device of claim 1 wherein said device body has perforations to allow a user to tear away a portion of said device body, thereby releasing said vacuum.

31. The urinary incontinence device of claim 1 wherein said device body has an aperture, and wherein said device further comprises a removable membrane, said removable membrane being attached to said external surface of said device body, completely covering said aperture in said device body, and being removable by a user to release said vacuum.

32. The urinary incontinence device of claim 1 wherein said device further comprises at least two interlocking members located within said cavity and attached to said internal surface of said device body, said at least two interlocking members being shaped to interlock upon at least partial compression and re-expansion of said device body, thereby preventing complete re-expansion of said device body.

33. The urinary incontinence device of claim 1 wherein said device body has an aperture, said device further comprising:
   a removable membrane removably attached to said device body and completely covering said aperture,
   a first interlocking member attached to said internal surface of said device body;
   a second interlocking member located within said device body cavity and attached to said removable membrane;
   wherein said first interlocking member and said second interlocking member are shaped to interlock upon at least partial compression and re-expansion of said device body, thereby detaching at least a portion of said removable membrane from said device body and releasing said vacuum.

34. The urinary incontinence device of claim 1 wherein said device body has an aperture, and wherein said device further comprises a soluble plug located within said aperture, said soluble plug completely preventing air flow through said aperture.

35. The urinary incontinence device of claim 1 wherein said device has a channel within said device body, said channel having a first opening and a second opening, and wherein said device further comprises:
   an air valve mechanism located within said channel; and
   an inflatable balloon apparatus located within said cavity and attached to said first opening of said channel,
      wherein said air valve mechanism permits unidirectional air flow through said air valve mechanism, and
   wherein when said device body is compressed and expands, air enters said channel through said second opening, passes through said channel and inflates said balloon apparatus.

36. A female urinary incontinence device comprising:
   a resilient and at least partially flexible device body defining a cavity having an opening, said device body having all internal surface and an external surface and an aperture; and
   a removable membrane removably attached to said external surface of said device body, completely covering said aperture in said device body,
   wherein when said urinary incontinence device is adapted to be positioned on said user's body, at least partial compression of said device body produces a vacuum within said cavity sufficient to hold said urinary incontinence device onto said user's body and wherein said membrane is removable by said user to release said vacuum.

37. The urinary incontinence device of claim 36 wherein said device body further comprises a ceiling and said aperture is located in said ceiling.

38. The urinary incontinence device of claim 36 wherein said removable membrane is attached to said device body with an adhesive.

39. The urinary incontinence device of claim 36 wherein said device body and said removable membrane are composed of two different grades of silicone rubber having different stiffness.

40. A female urinary incontinence device comprising:
  a resilient and at least partially flexible device body defining a cavity having an opening, said device body having an internal surface, an external surface and an aperture;
  a removable membrane removably attached to said device body and completely covering said aperture;
  a first interlocking member attached to said internal surface of said device body; and
  a second interlocking member located within said device body cavity and attached to said removable membrane,
  wherein when said urinary incontinence device is adapted to be positioned on said user's body, at least partial compression of said device body produces a vacuum within said cavity sufficient to hold said urinary incontinence device onto said user's body,
  wherein said first interlocking member and said second interlocking member are shaped to interlock upon at least partial compression and re-expansion of said device body, thereby detaching at least a portion of said removable membrane from said device body and releasing said vacuum.

41. The urinary incontinence device of claim 40 wherein said removable membrane is attached to said internal surface of said device body.

42. The urinary incontinence device of claim 40 wherein said removable membrane is attached to said external surface of said device body.

43. A female urinary incontinence device comprising:
  a resilient and at least partially flexible device body defining a cavity having an opening, said device body having an internal surface and an external surface and an aperture; and
  a soluble plug located within said aperture, said soluble plug completely preventing air flow through said aperture,
  wherein when said urinary incontinence device is adapted to be positioned on said user's body, at least partial compression of said device body produces a vacuum within said cavity sufficient to bold said urinary incontinence device onto said user's body.

44. The urinary incontinence device of claim 43 wherein said water soluble plug substantially dissolves upon contact with water.

45. A method for alleviating urinary incontinence of a female user comprising the steps of:
  applying a urinary incontinence device onto the meatus of the user's body, said urinary incontinence device comprising:
    a resilient and at least partially flexible device body defining a cavity having an opening, said device body having an internal surface and an external surface; and
    at least one urethra obstructing member attached to said device body, said urethra obstructing member being shaped to deform the urethra of the user's body and to cause said urethra to be substantially obstructed; and
  positioning said urinary incontinence device on the user's body by compressing said device body to produce a vacuum within said cavity to hold said device onto the user's body.

46. The method of claim 45 wherein said urinary incontinence device applying step comprises the step of applying said device over the urethra of the user.

47. The method of claim 45 wherein said urinary incontinence device applying step comprises the step of applying said device on the anterior vaginal wall of said user along a path of the urethra.

48. The method of claim 45 wherein said urinary incontinence device applying step comprises the step of applying said device onto the meatus of the user's body, the urinary incontinence device comprising at least one urethra obstructing member shaped to cause said urethra to be completely obstructed.

49. A female urinary incontinence device comprising:
  a resilient and at least partially flexible device body defining a cavity having an opening, said device body having an internal surface and an external surface and being adapted to be positioned on the meatus of a user's body, said device body being constructed of a material permitting a limited number of compressions, wherein said device body includes a releasable portion to assist removal of said device from the meatus of the user's body.

50. The female urinary incontinence device of claim 49 wherein said device body is constructed of a material selected from the group consisting of thermoplastic elastomers and urethanes.

51. The female incontinence device of claim 49 wherein said device body is constructed from silicone.

52. A female urinary incontinence device, comprising:
  a device body defining a cavity with an aperture and a body-contacting portion around the aperture, said device capable of maintaining a vacuum in the cavity when the body-contacting portion is in contact with a meatus and further including a releasable portion to assist removal by venting said vacuum.

53. The device of claim 52 wherein said releasable portion is irreversibly releasable, preventing reuse of the device.

54. The device of claim 52 wherein said releasable portion is tearable.

55. The device of claim 54 wherein said releasable portion is defined by perforations.

56. The device of claim 55 wherein said device body includes a chamber portion defining said cavity and a flange portion surrounding said opening.

57. The device of claim 56 wherein said releasable portion is on said chamber portion.

58. The device of claim 56 wherein said releasable portion is on said flange.

59. The device of claim 54 wherein said releasable portion is defined by slits.

60. A method of treating female urinary incontinence, comprising the steps of:
  providing a device having a device body defining a cavity with an aperture and a body-contacting portion around the aperture,
  applying said device to the meatus by positioning the body-contacting portion in contact with a meatus and creating a vacuum in said cavity;

breaching a portion of the device to release said vacuum in said cavity; and removing said device from the meatus.

61. The method of claim 60 comprising breaching a portion of the device by tearing.

62. The device of claim 60 wherein said breaching step comprises the step of preventing said device from being reused.

* * * * *

UNITED STATES PATENT AND TRADEMARK OFFICE
CERTIFICATE OF CORRECTION

PATENT NO : 5,813,973
DATED : September 29, 1998
INVENTOR(S): David Gloth

It is certified that error appears in the above-identified patent and that said Letters Patent is hereby corrected as shown below:

Col. 14, line 15 (Claim 1) delete "means" and replace it with --meatus--.

Col. 18, line 35 (Claim 51) insert --urinary-- after "female".

Signed and Sealed this

Fourteenth Day of March, 2000

Attest:

Attesting Officer

Q. TODD DICKINSON

Commissioner of Patents and Trademarks